US011586276B2

United States Patent
Winold et al.

(10) Patent No.: US 11,586,276 B2
(45) Date of Patent: Feb. 21, 2023

(54) SYSTEMS AND METHODS FOR GENERATING COMPLEMENTARY DATA FOR VISUAL DISPLAY

(71) Applicant: PENUMBRA, INC., Alameda, CA (US)

(72) Inventors: Hans Winold, Berkeley, CA (US); Joseph White, Oakland, CA (US); Ryan Corniel, San Jose, CA (US); Mark Samuel Gutentag, San Francisco, CA (US); John Lockhart, San Ramon, CA (US)

(73) Assignee: PENUMBRA, INC., Alameda, CA (US)

( * ) Notice: Subject to any disclaimer, the term of this patent is extended or adjusted under 35 U.S.C. 154(b) by 0 days.

(21) Appl. No.: 17/276,548

(22) PCT Filed: Jul. 22, 2019

(86) PCT No.: PCT/US2019/042857
§ 371 (c)(1),
(2) Date: Mar. 16, 2021

(87) PCT Pub. No.: WO2020/060666
PCT Pub. Date: Mar. 26, 2020

(65) Prior Publication Data
US 2022/0035443 A1 Feb. 3, 2022

Related U.S. Application Data

(60) Provisional application No. 62/734,824, filed on Sep. 21, 2018.

(51) Int. Cl.
*G06F 3/01* (2006.01)
*G06T 19/00* (2011.01)

(52) U.S. Cl.
CPC .............. *G06F 3/011* (2013.01); *G06T 19/00* (2013.01)

(58) Field of Classification Search
None
See application file for complete search history.

(56) References Cited

U.S. PATENT DOCUMENTS

2012/0327194 A1* 12/2012 Shiratori ................. G06F 3/011
348/47
2015/0309535 A1 10/2015 Connor
(Continued)

FOREIGN PATENT DOCUMENTS

| CN | 106471544 A | 3/2017 |
|----|-------------|--------|
| EP | 2672228 B1  | 1/2017 |

(Continued)

OTHER PUBLICATIONS

Aristidou, Andreas, et al., "FABRIK: A fast, iterative solver for the Inverse Kinematics problem", Graphical Models 73 (2011), pp. 243-260.

(Continued)

*Primary Examiner* — Aneeta Yodichkas
(74) *Attorney, Agent, or Firm* — Haley Guiliano LLP

(57) ABSTRACT

A system for generating complementary data for a visual display that includes one or plurality of wearable sensors that collect tracking data for a users position, orientation, and movement. The sensor(s) are in communication with at least one processor that may be configured to receive tracking data, identify missing tracking data, generate complementary data to substitute for missing tracking data, generate a 3D model comprised of tracking data and complementary data, and communicate the 3D model to a display. Complementary tracking data may be generated by (Continued)

comparison to a key pose library, by comparison to past tracking data, or by inverse kinematics.

14 Claims, 8 Drawing Sheets

(56) References Cited

U.S. PATENT DOCUMENTS

| | | |
|---|---|---|
| 2015/0339910 A1 | 11/2015 | Stenzler |
| 2016/0259404 A1* | 9/2016 | Woods .................... G06F 3/012 |
| 2017/0025026 A1 | 1/2017 | Ortiz Catalan |
| 2018/0070864 A1 | 3/2018 | Schuster |
| 2018/0122125 A1* | 5/2018 | Brewster ................ G06T 13/40 |
| 2018/0357472 A1 | 12/2018 | Dreessen |

FOREIGN PATENT DOCUMENTS

| | | |
|---|---|---|
| JP | 2011095935 A | 5/2011 |
| WO | 2011142084 A1 | 11/2011 |

OTHER PUBLICATIONS

Cole, "Virtual and Augmented Reality, Phantom Experience, and Prosthetics" Psychoprosthetics, 141-153 (2008).

Jiang et al., "Real-time full-body motion reconstruction and recognition for off-the-shelf VR devices," Proceedings of the 15th ACM SIGGRAPH Conference on Virtual-Reality Continuum and its Applications in Industry, 1:309-318 (2016).

Macpeople, Kadokawa Corporation, 10(20):138-41 (2014).

Computer English Language Translation of Japanese Reason for Refusal in Japanese Patent Application No. 2021-516382, dated Jun. 27, 2022 (4 pages), which includes a concise statement of the relevance of MacPeople, Kadokawa Corporation, 10(20):138-41 (2014).

* cited by examiner

SYSTEMS AND METHODS FOR GENERATING COMPLEMENTARY DATA FOR VISUAL DISPLAY

CROSS-REFERENCE

This application is a national stage application under 37 U.S.C. § 371 of International Application PCT/US2019/042857, filed Jul. 22, 2019, which claims the benefit of U.S. Provisional Patent Application No. 62/734,824, filed Sep. 21, 2018, which are incorporated herein by reference in their entireties.

BACKGROUND

Virtual reality (VR) strives to create an immersive virtual world that generates the perception of being physically present in a virtual world. Immersion depends on surrounding the player with believable images, sounds, and other stimuli. Believable, life-like stimuli elicit a state of consciousness featuring a partial or complete suspension of disbelief that enables action and reaction to stimulations in the virtual environment.

However, a lack of synchronization between the player's own movements and the avatar's movements reduces the player's sense of immersion. Since perfect motion tracking is not typically a realistic option for most game applications, games may animate an avatar, or portion thereof, where the movements of the avatar do not necessarily correlate to the player's own movements. Missing data may be an issue where tracking data is permanently or temporarily lacking. For instance, a tracking system may track some body parts and not others, may miss frames, may comprise fewer or in appropriately placed sensors than can enable realistic tracking, etc.

For example, games animating an avatar often animate hands for the player to use as his or her own; however, the animated hands may or may not possess realistic shape or motion. Animated hands provide base-line immersion, because, like in everyday life, the part of our bodies we see the most frequently are our hands. As such, a replication of hands within a virtual world suffers increased visual scrutiny from a player. At least one challenge with hands is animating the complex movements fingers are capable of in real-time. Providing realistic and intuitive finger movements is an important step towards achieving an improved immersive experience.

Another challenge is eliciting a suspension of disbelief when animating a full-bodied avatar for an amputee. If a hand, arm, leg, or foot is amputated due to accident or disease, eight out of ten amputees experience a feeling of discomfort in the limb that is no longer there. The phenomenon is called phantom limb pain. Tests have shown that phantom limb pain can be relieved if the brain is tricked into thinking that the amputated limb is still attached to the body. Thus, the generation of an immersive avatar may be useful in addressing phantom limb pain.

Outside of VR, a related challenge is achieving an immersive prosthetic. The more accurately a prosthetic limb responds to a user's commands, the more natural and satisfactory the prosthetic appears. As such, improvements in the movements of prosthetic limbs can help promote a sense of self-identity with a prosthetic.

SUMMARY

The present invention generally addresses the issue of missing or inadequate data when tracking human movements. The present invention analyzes the movements of tracked body parts and determines complementary movements for adjacent body parts that may lack adequate tracking data. Complementary movement data is then combined with tracking data for display. In one example, the system collects tracking data for some of a user's body parts, generates complementary movement data for the remainder of the user's body parts, and then animates an avatar that moves according to a combination of tracking data and complementary tracking data. Complementary tracking data may transcend joints and be generated without a corresponding end effector.

One application of interest is tracking wrist movement, generating complimentary finger movements, and animating an avatar with both movements. A second application of interest is tracking movement near an amputated limb, determining what complementary movements would have been made by the missing limb if it was still attached, and then either animating such movements onto a full-bodied avatar or causing a prosthetic to perform such movements. A third application of interest is combining tracking data and system generated complementary movement data for the same body part and using that combination to improve avatar animation accuracy and precision.

In some embodiments, the present disclosure is comprised of one or a plurality of wearable sensors disposed on a user, wherein the wearable sensors collect and transmit tracking data; a processor in communication with a memory that includes processor executable instructions, wherein the execution of the instructions cause the system to at least: receive tracking data; identify missing tracking data; generate complementary tracking data to substitute for at least a portion the missing tracking data; map the tracking data and complementary tracking data onto a 3D model, wherein the 3D model is a virtual representation of the user; and communicate the 3D model for display. Such a system may generate complementary tracking data by comparing partial tracking data to a key pose library, by matching partial tracking data to a cluster of prior 3D models communicated for display, or with inverse kinematics.

In an aspect, the present disclosure provides a system for generating complementary tracking data. The system may comprise: one or a plurality of wearable sensors configured to be disposed on a subject, wherein the wearable sensors are configured to collect and transmit tracking data; a processor in communication with a memory that includes processor executable instructions, wherein the execution of the instructions cause the system to: (a) receive tracking data from the one or the plurality of wearable sensors; (b) map the tracking data onto a 3D model, wherein the 3D model is a virtual representation of an extent and a motion of the subject; (c) identify an incomplete portion of the 3D model, the incomplete portion comprising a portion of the model not mapped to the tracking data; (d) generate complementary tracking data to substitute for at least a portion of the incomplete portion; and (e) include the complementary tracking data in the 3D model.

In some embodiments, the complementary data is generated by comparing available tracking data to a key pose library. In some embodiments, tracking data is compared to blend spaces between two or more key poses in the key pose library. In some embodiments, tracking data is compared to key poses of the library of key poses to determine a strongest match. In some embodiments, the determination of a match weights similarities of joints and body parts closest to the incomplete portion more heavily than joints and body parts distant from the incomplete portion. In some embodiments, the memory includes processor executable instructions that cause the system to access one or a series of prior 3D models, wherein the prior 3D models were previously communicated for display.

In some embodiments, the complementary tracking data is generated by identifying a cluster of repetitive tracking data among a series of prior 3D models, matching tracking data to the cluster, and generating complementary data similar to the matched portion of the cluster. In some embodiments, the complementary tracking data is generated by identifying a cluster of repetitive tracking data among a series of prior 3D models, determining where available tracking data best fits in the cluster of repetitive tracking data, and generating complementary tracking data that mimics the cluster of repetitive tracking data. In some embodiments, the processor is configured to analyze the one or a series of prior 3D models for gesture triggers, wherein the identification of a gesture trigger causes the system to communicate a series of updated 3D models that are at least partially blended with a pre-recorded gesture animation.

In some embodiments, the complementary tracking data is generated with a FABRIK solver when tracking data for an end effector is available and with a cluster function or key pose match when tracking data for an end effector is unavailable. In some embodiments, the memory includes processor executable instructions that cause the system to generate complementary tracking data for portions of the 3D model for which the system did receive tracking data. In some embodiments, the 3D model is updated by blending the complementary tracking data and the tracking data.

In some embodiments, the one or a plurality of wearable sensors are comprised of electromagnetic receivers and emitters, one or more optical elements, infrared emitters, accelerometers, magnetometers, gyroscopes, or a combination thereof. In some embodiments, the processor receives tracking data from both electromagnetic sensors and one or more cameras. In some embodiments, the wearable sensors are wireless and communicate with a radio frequency. In some embodiments, the system further comprises one or more straps wearable by a user, wherein the one or a plurality of wearable sensors are configured to be disposed in or on the one or more straps. In some embodiments, the display is configured to display the updated 3D model physically, in virtual reality, or in mixed reality. In some embodiments, the tracking data includes wrist or metacarpus tracking data that is used to determine complementary tracking data for fingers of the 3D model. In some embodiments, the tracking data is separated from the complementary tracking data by at least one joint of the user. In some embodiments, the processor receives tracking data for "n" body parts of the user, and the processor communicates for display an updated 3D model with "n+1" body parts.

In another aspect, the present disclosure provides a system for generating complementary tracking data. The system may comprise a processor in communication with a memory that includes processor executable instructions, the instructions comprising: a set of tracking data, wherein the tracking data relates to the position or motion of one or more parts of the user; a 3D model, wherein the 3D model is a virtual representation of an extent and a motion of a user; a library, wherein the library comprises a set of poses, gestures, or both; a set of complementary tracking data, wherein the set of complementary tracking data comprises a least a portion of at least one selected pose or gesture from the library; a combined model, the combined model comprising the set of tracking data and the set of complementary data.

In some embodiments, the complementary data includes a limb, appendage, joint, or digit not present in the set of tracking data. In some embodiments, the complementary data includes a period of motion not present in the set of tracking data. In some embodiments, a comparison of the library to the set of tracking data is used to select the pose or gesture from the library. In some embodiments, the instructions further comprise a learning algorithm, wherein the set of complementary data is generated by the learning algorithm. In some embodiments, the instructions further comprise a learning algorithm, wherein the pose or gesture is selected by the learning algorithm. In some embodiments, the complementary data is generated by a comparison of the set of tracking data to a key pose library. In some embodiments, the comparison comprises spaces between two or more key poses in the key pose library and the complementary data is generated to blend between those spaces.

In some embodiments, the set of tracking data is mapped to the 3D model by a comparison of the tracking data to a set of key poses within the library of key poses to determine a match. In some embodiments, the match is determined by weighting similarities of joints and body parts closest to the incomplete portion more heavily than joints and body parts distant from the incomplete portion. In some embodiments, the instructions comprise one or a series of prior poses, gestures, or both of the motion of the user. In some embodiments, the complementary tracking data is generated by identifying a cluster of repetitive tracking data among the series of prior poses, gestures, or both; matching the set of tracking data to the cluster; and generating complementary data similar to the matched portion of the cluster. the complementary tracking data is generated by identifying a cluster of repetitive tracking data among the series of prior poses, gestures, or both; determining where available tracking data fits in the cluster of repetitive tracking data; and generating complementary tracking data that mimics the cluster of repetitive tracking data. In some embodiments, the instructions comprise an analysis of a least a portion of the series of prior poses, gestures, or both for gesture triggers, wherein the identification of a gesture trigger causes the system to communicate a series of updated sets of merged data that are at least partially blended with a pre-recorded gesture animation.

In some embodiments, complementary tracking data is generated with a FABRIK solver when tracking data for an end effector is available and with a cluster function or key pose match when tracking data for an end effector is unavailable. In some embodiments, the set of tracking data includes wrist or metacarpus tracking data that is used to determine complementary tracking data for fingers of the 3D model. In some embodiments, the set of tracking data is separated from the complementary tracking data by at least one joint. In some embodiments, the set of tracking data comprises tracking data for "n" body parts, and the complementary data is mapped to the 3D model to form an combined model with "n+1" body parts. In some embodiments, the combined model is generated in near live time, communicated for at least partial display to the user, or both.

In another aspect, a system for generating complementary data for a visual display is provided. The system may comprise: (a) one or more electromagnetic emitters and one or more electromagnetic sensors configured to be selectively placed on one or more tracked body parts; and (b) at least one processor in communication with the visual display, the one or more electromagnetic emitters, and the one or more electromagnetic sensors and configured to receive tracking data from the one or more electromagnetic emitters and the one or more electromagnetic sensors, and to generate complementary display data comprising projected motion not within the tracking data and based upon a library of potential motions.

In some embodiments, the processor is further configured to display movement and position of the one or more tracked body parts on the visual display using the tracking data. In some embodiments, the system further comprises one or more straps wearable by a user, wherein the one or more emitter and the one or more sensors are configured to be disposed in or on the one or more straps. In some embodiments, the system further comprises one or more optical elements, wherein the optical elements are wearable by a user and wherein the one or more optical elements comprise infrared emitters, accelerometers, magnetometers, gyroscopes, or a combination thereof. In some embodiments, the processor is configured to process 3-D graphics using (1) a puppet skeleton rig animation technique, (2) a vertex animation solution, or (3) a combination of both (4) to generate the complementary display data. In some embodiments, the processor is further configured to combine the tracking data and the complementary display data in 3-D graphics, wherein the 3-D graphics comprise a model of either an avatar or a prosthetic, and wherein the model is transferred from the processor as processed movement data.

In some embodiments, the display is configured to display the complementary display data physically, in virtual reality, or in mixed reality. In some embodiments, the processor is further configured to generate complementary display data for one or more tracked body parts. In some embodiments, the tracking data includes wrist tracking data and the complementary display data includes finger movement data, and wherein a series of one or more wrist or metacarpus positions and movements are analyzed to determine complementary movements of one or more fingers. In some embodiments, the processor is configured to generate 3-D graphics for the one or more tracked body parts, one or more untracked body parts, or both, wherein the one or more tracked or untracked body parts comprises fingers, hands, elbows, shoulders, head, torso, waist, thighs, shins, feet, toes, wherein the tracking data from one or more tracked body parts is processed to generate complementary movement data for a second one or more tracked body parts, for untracked body parts, or a combination of both. In some embodiments, the processor is configured to generate 3-D graphics for a wrist, hand, and set of fingers by analyzing tracking data from a player's wrist or metacarpus. In some embodiments, the processor is configured (i) to analyze tracking data from a wrist over a period of time, (ii) to determine whether a pre-defined movement pattern of the wrist has been executed, (iii) to generate a thematic gesture for the wrist, hand, and set of fingers based on the identification of the pre-defined movement pattern, wherein the thematic gesture comprises waving, pointing, or palm opening, and (iv) to generate a 3-D graphic or series of 3-D graphics on the display comprising the thematic gesture.

In another aspect, a method for tracking movement of a subject and displaying an avatar is provided. The method may comprise: (a) tracking movement of one or more tracked body parts of a subject with one or more electromagnetic emitters and one or more electromagnetic sensors; (b) receiving tracked movement data for the one or more tracked body parts from the one or more electromagnetic emitters and one or more electromagnetic sensors; (c) analyzing tracked movement data to determine complementary movement data for one or more body parts nearby or adjacent to the one or more tracked body parts; and (d) animating tracked movement data and complementary movement data onto an avatar.

In another aspect, a method for animating an avatar is provided. The method may comprise: (a) receiving tracked movement data comprising position, movement, or both of one or more tracked body parts; (b) determining complementary movement data for one or more body parts nearby or adjacent to the one or more tracked body parts through analysis of the tracked movement data; and (c) animating tracked movement data and complementary movement data onto an avatar.

In some embodiments, the complementary movement data is separated from the tracked movement data by at least one joint. In some embodiments, the tracked movement data includes a wrist or metacarpus, and the complementary movement data includes a hand, one or more fingers, or both. In some embodiments, the step of tracking movement of the one or more tracked body parts comprises tracking a number of body parts "n", and the step of animating body parts comprises animating a number of body parts "n+1". In some embodiments, the step of analyzing the tracked movement data to determine complementary movement data further comprises analyzing a second one or more body parts near to the one or more body parts, and animating a combination of tracked movement data and complementary movement data onto an avatar.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
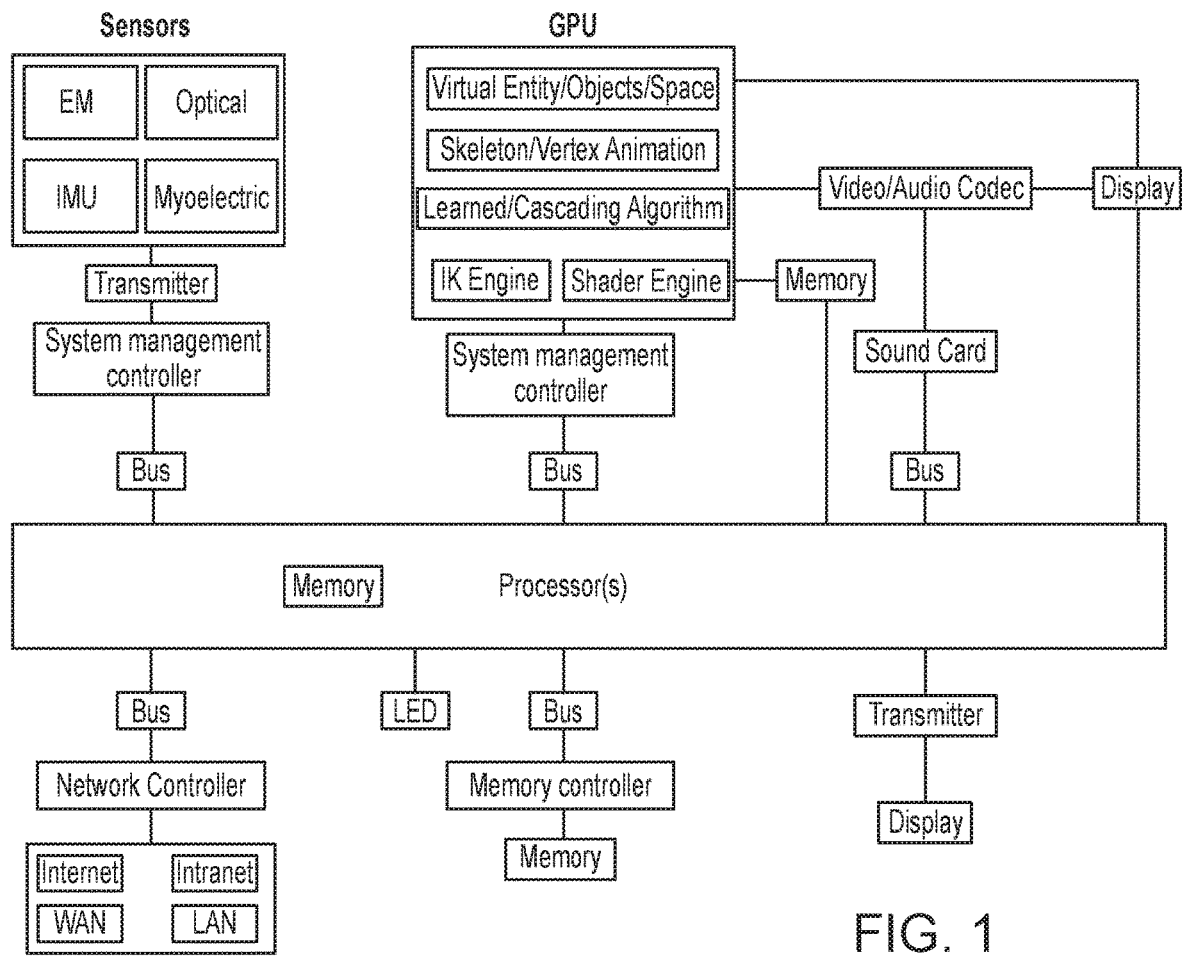
FIG. 1 illustrates an example computing environment in accordance with some embodiments.

A player "becomes" their avatar when they log into a virtual reality ("VR") game. When the player tells their body to move, they see their avatar move accordingly. If a system achieves perfect tracking and the player's limb count is equivalent to the avatar's limb count, then the player's movements can be perfectly mapped onto an avatar, which thereby enables improved immersion. On the other hand, if the avatar has more limbs than the player or if perfect tracking is even temporarily lacking, then improved immersion is achieved by displaying tracked movements in combination with realistic complimentary movements in the places where tracking data is lacking. Aspects of the present disclosure provide such a function.

To be immersive, the system generated limb may ideally be responsive. The player's intentions and volitions may be translated into limb movements. The limb may appear to follow the laws of physics, such as by making sounds and being interactive with the virtual environment. All of this may be done with animations that are derivative of and proportional to trackable movements.

There are at least two general approaches to hand animation. In a first approach, an avatar is animated with hands and a portion of the forearms. The hand may be generally animated in a neutral position, which remains static as the player traverses the virtual world. When the player interacts with an object or presses a button on a controller, the hand may snap shut, e.g. to grasp an object. Examples of such VR games include, Doom, Rift Core 2.0, Occulus Unity, and Surgeon Simulator. A similar approach is used by Bethesda's Skyrim VR game. However, that game includes specific hand animations for casting spells (palms facing forward with fingers splayed) and running (fingers curl in slightly). These solutions offer rudimentary hand animations, and thus fail to optimally provide an immersive experience.

In a second approach, a player's hands and fingers may be actively tracked and displayed on an avatar. Systems such as Noitom Hi5 tracker gloves and VRgluv are worn on the hands to provide tracking and haptic feedback. These solutions can be prohibitively data intensive, cumbersome, and expensive. Systems such as Leap Motion and Playstation move Heroes track finger movements with optical cameras. Optical tracking systems can be prohibitively data intensive, and such systems generally suffer from poor fidelity, limited range, and/or line of sight challenges. Microsoft patents U.S. Pat. Nos. 9,861,886, 9,824,478, and 8,451,278 disclose optical tracking techniques with similar drawbacks.

With regard to animating movements for an amputated limb, there may be several solutions. A first solution uses a mirror. By placing a mirror at an angle in front of the chest one can create the visual illusion that the body is symmetrical. If one pretends to do the same movements simultaneously with both hands, the brain in many cases can be convinced that it is in contact with an amputated hand. Such a technique suffers from poor verisimilitude of sensory feedback from the missing limb, and the apparatus is crude and the illusion is often not compelling (i.e. not immersive).

A second solution tracks an intact portion of a limb and then animates a full limb (see "Immersive Low-Cost Virtual Reality Treatment for Phantom Limb Pain: Evidence from Two Cases" by Ambron et al.). In the Ambron study, a participant with a transradial amputation (below-the-knee) had the remaining portion of the shin tracked, whereby a full shin and foot were animated; however, while the animations included movements of the shin relative to the thigh, they did not disclose a foot movement animations.

In a third approach, a user's amputated limbs may be animated according to Electromyography ("EMG") signals produced at or near the amputated limb's "stump." When properly executed, the user can use their thoughts alone to control the movements of the amputated limb on an in-game avatar (or a prosthetic). Such an approach suffers from prolonged setup time. The setup requires placing and replacing electrodes until maximum signal amplitudes are found. The setup typically requires teaching a learning algorithm to interpret the user's particular EMG signals, whereby the learned algorithm can ultimately translate raw EMG signals into movement data. To teach the algorithm, for example, the user may be requested to attempt to make various hands shapes over and over, and the learning algorithm uses these instances of attempted movement as training data. This approach also faces several fundamental challenges. This technique depends on a user's EMG skill (how well a user can control their EMG signals) and how reliably the electrodes can pick up the signals.

Aspects of the present disclosure provide improved representation of the movements of a user when motion tracking data is insufficient or absent. Aspects of the present disclosure may offer one or more solutions to the missing data problem when tracking a person's movements. Systems and methods of the present disclosure may take available tracking data and generate complementary movement data where tracking data may be permanently or temporarily, completely or partially lacking. Systems and methods of the present disclosure may animate or display movements according to the tracked movement data and complementary movement data. In some cases, systems and methods of the present disclosure may foster a sense of self-identity with a representation of the player (e.g. an avatar) or portion thereof (e.g. partial avatar or prosthetic). To achieve this, the representation of the player may be visually realistic and it may appear to be reliably responsive to the player's volitions and commands.

At least one challenge of the missing data problem may be to accurately analyze tracking data for body parts on one side of an articulating joint to predict movements of body parts on the other side of the joint. In some embodiments, the present disclosure meets this challenge with a combination of skeletal and vertex animation techniques. In some embodiments, the present disclosure provides a learned algorithm and/or cascading algorithm to model tracked movements and predict complementary movements. In instances where tracking data is lacking across a joint, aspects of the present disclosure may animate movements for body parts on both sides of the joints without using an end effector.

The present disclosure offers one or more animation solutions for fingers that are capable of leaving the player's hands free from a glove, handheld controller, or similar tool that covers the fingers and/or restricts finger movements. In some embodiments, the present disclosure offers an animation solution for fingers that does not track finger movements with cameras. In some embodiments, this solution may utilize movements fingers make as a person bends and twists his or her wrist or metacarpus. Such finger movements may mimic the natural movements or automatic movements of the fingers and wrist. Systems and methods of the present disclosure display this finger movement and thereby provide increased feelings of immersion and visual enhancement. In some embodiments, pre-defined wrist or metacarpus motions and movement patterns may trigger specific gestures, such as pointing, waving, or opening the palm.

In some embodiments, systems and methods of the present disclosure may utilize tracking data from body parts near the elbows, knees, feet, and toes in order to generate complimentary movement animations for the elbows, knees, feet, and/or toes. For example, tracking data from the elbow may be used to generate complementary data of the forearm and/or wrist and/or fingers. For example, tracking data from the knees may be used to generate complementary data of the calf and/or ankle and/or toes. For example, if tracking data for a particular body part is inadequate or lacking, the tracking data from a nearby body part or parts may be used to determine or predict the proper movements or gestures to animate.

Systems and methods of the present disclosure offer at least some solutions to amputated limb animation that is immersive, transcends joints, and requires minimal setup. Tracking data near the stump may be used to predict what movements the limb would likely have made. Such movements may then be animated onto an avatar or used to influence the movements of a prosthetic.

Part 1: Avatar Animation Techniques

Computing Environment

Figure 3:
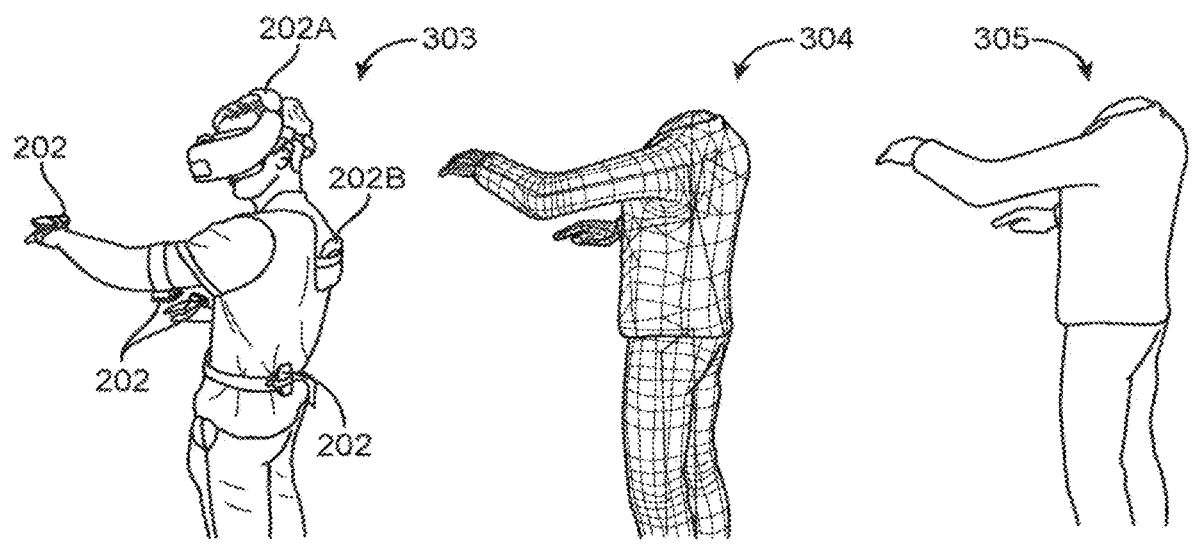
FIG. 3 illustrates an animation pipeline from sensor data collection, to 3D modeling, to avatar animation, in accordance with some embodiments.

Aspects of the present disclosure provide a computing environment capable of tracking, modeling, and displaying a visual representation of a user. FIG. 1 illustrates an example computing environment, in accordance with some embodiments. The computing environment may comprise one or more printed circuit boards (PCBs). The computing environment may function as a single device or across several devices and, in some cases, is comprised of one or more printed circuit boards. In general terms, the computing environment may track, model, and display a visual representation of a user or a subject in physical space or virtual space. The computing environment may track a user or a subject surroundings and movements in physical space. The computing environment may generate a 3-D model of the user in virtual space. The computing environment may display a visual representation of the model for the user, as depicted in FIG. 3. For instance, the visual representation may be an avatar displayed on a screen, where the avatar's motion is controlled by the user. The computing environment may map a user's motion in the physical space to the avatar's motion in virtual space.

The computing environment may include software and hardware components that enable execution of applications that allow a user and/or the computing environment to play games and various types of media. The software may allow the user and/or computing environment to control and manipulate non-game applications and operating systems. The computing environment may include one or more sensors, processors, graphic processing units (GPU), video encoder/video codec, sound cards, transmitter modules, network interfaces, and light emitting diodes (LED). These components may be housed on a local computing system or may be remote components in wired or wireless connection with a local computing system (e.g. a remote server, a cloud, a mobile device, a connected device, etc.). Connections between components may be facilitated by one or more buses (e.g. peripheral component interconnects (PCI) bus, PCI-Express bus, or universal serial bus (USB)). With such buses, the computing environment may be capable of integrating numerous components, numerous PCBs, numerous remote computing systems. One or more system management controllers may provide data transmission management functions between the buses and the components they integrate. Such management controllers may facilitate the computing environment's orchestration of these components that may each utilize separate instructions within defined time frames to execute applications. The network interface may include an Ethernet connection or a component that forms a wireless 802.11b, g, a, or n connection to a local area network (LAN), wide area network (WAN), intranet, or internet.

Sensor(s)

Figure 2A:
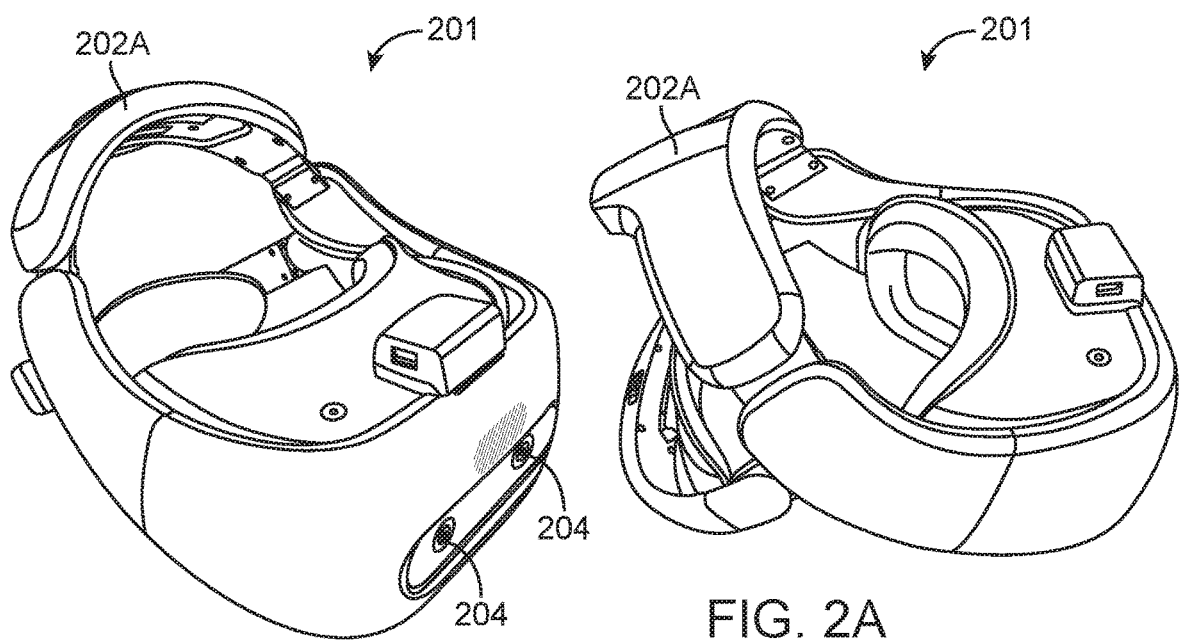
FIG. 2A illustrates a head mounted display, in accordance with some embodiments.
Figure 2B:
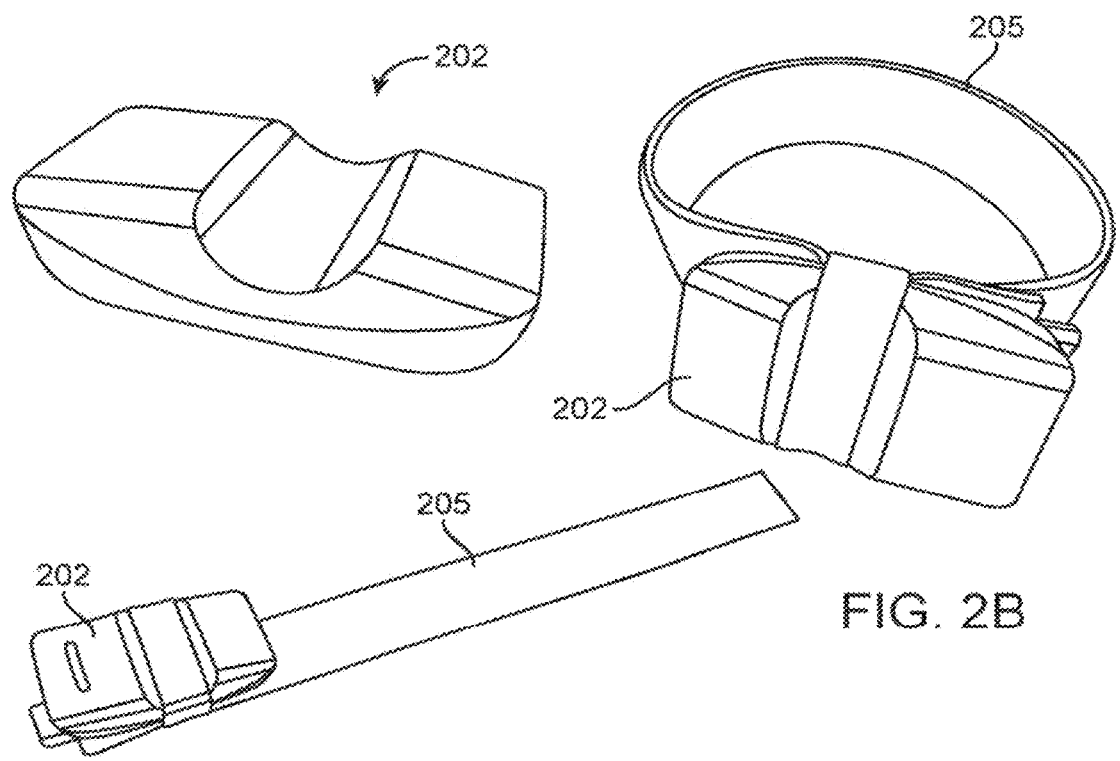
FIG. 2B illustrates wearable sensors capable of tracking a user's movements, in accordance with some embodiments.

FIG. 2A and FIG. 2B illustrate examples of a head mounted display (HMD) 201 and wearable sensors 202 capable of tracking a user's movements. In some embodiments, systems and methods of the present disclosure may use electromagnetic tracking, optical tracking, infrared tracking, accelerometers, magnetometers, gyroscopes, myoelectric tracking, other tracking techniques, or a combination of one or more of such tracking methods. The tracking systems may be parts of a computing system as disclosed herein. The tracking tools may exist on the one or more PCBs where they may monitor one or more users to perform one or more functions such as: capture, analyze, and/or track a subject's movement. In some cases, the system may utilize more than one tracking method to improve reliability, accuracy, and precision.

Electromagnetic tracking may be enabled by running alternating current through one or more ferrite cores with three orthogonal (x, y, z) coils, thereby transmitting three dipole fields at three orthogonal frequencies. The alternating current generates a dipole, continuous wave electromagnetic field. With multiple ferrite cores, differentiation between cores may be achieved using frequency division multiplexing. U.S. Pat. Nos. 8,520,010 & 10,162,177 provide additional details. The cores may function to emit and/or receive EM signals from each other, ferrous objects around the user, and/or the earth's magnetic field to determine the position and orientation of the core and thus the sensor.

Tracking may be further enabled by inertial measurement units (IMUs). IMUs may include accelerometers, magnetometers, and gyroscopes. Accelerometers measure the rate of change of the velocity of a given PCB undergoing movement in physical space. Magnetometers characterize magnetic field vectors by strength and direction at a given location and orientation. Gyroscopes utilize conservation of angular momentum to determine rotations of a given PCB. The individual components of an IMU serve to supplement, verify, and improve the tracking data captured by electromagnetic sensors. In one example, the wearable sensors 202 utilize a combination of electromagnetic tracking and IMU tracking to capture, analyze, and track a user's movements.

Optical tracking and infrared tracking may be achieved with one more capture devices. In some embodiments, the system may perform tracking functions using a combination of electromagnetic tracking and optical tracking. In some cases, a camera is worn by the user. In some cases, capture devices may employ an RGB camera, time-of-flight analysis, structured light analysis, stereo image analysis, or similar techniques. In one example of time-of-flight, the capture device emits infrared (IR) light and detects scattered and reflected IR light. By using pulsed IR light, the time-of-flight between emission and capture for each individual photon indicates the distance the photon traveled and hence the physical distance of the object being imaged. This may allow the camera to analyze the depth of an image to help identify objects and their locations in the environment.

Similar techniques may analyze reflected light for phase shifts, intensity, and light pattern distortion (such as bit maps). Stereo image analysis utilizes two or more cameras separated by some distance to view a similar area in space. Such stereo cameras capture a given object at one or more angles, which enables an analysis of the object's depth. In one example, the HMD 201 utilizes one or more cameras 204 that enable optical tracking to identify an object or location in physical space to serve as an anchor, e.g. (0, 0, 0). The tracking system then determines global movements in reference to the anchor.

Myoelectric tracking may be achieved using multiple sensors capable of sensing nerve impulse (EMG) signals. The sensors may be attached with a band, with leads, or with a needle electrode. The EMG signals being decoded into a model of intended movements by a learned algorithm executed, at least, in part by a processor as discussed below. Monitoring EMG activity can be useful for measuring the neural activity associated with neuroplasticity.

In one specific example, the electromagnetic sensors each include a receiver (RX) module having three orthogonal coils that are configured to receive an electromagnetic field generated by a transmitter (TX), which also includes three orthogonal coils. The magnetic field data collected at each coil is processed by a Discrete Fourier Transformation (DFT). With three coils on each module, the signal received by a module is representable by a 3×3 signal matrix ("Sigmat"), which is a function of a transmitter-to-sensor radius vector and a transmitter-to-sensor rotation matrix (a.k.a. directional cosines or projection matrix). An IMU and camera system may be used to correct for errors in electromagnetic tracking. In one example, a dipole field approximation allows for the determination of position and orientation (PnO) according to Equation 1, as described in U.S. Pat. No. 4,737,794.

$$X = N^t B(r) \qquad \text{Equation 1}$$

X—3×3 Sigmat Matrix (as sensed in RX coordinates)
N—3×3 orthonormal orientation (in TX coordinates) Transmitter to sensor rotation matrix (6 values received from IMUs)
r—3×1 position vector (in TX coordinates) (transmitter to sensor radius vector)
B—3 magnetic fields at r as the columns of a 3×3 matrix (in TX coordinates)

Distortion and interference may be compensated for by adding E(r) to the equation. E(r) is a result calculated from the super position of the theoretic dipole fields and is represented as a 3×3 matrix of unknown magnetic field distortion or interference. E(r) may be described as an error matrix in that is compensates for errors in calculated PnO, as described in U.S. Pat. No. 9,459,124.

$$X = N^t(B(r) + E(r)) \qquad \text{Equation 2}$$

E(r) may be calculated using data from IMUs and a camera system (as explained in more detail below). Each IMU typically includes an accelerometer, a gyroscope, and a magnetometer. These components help correct for error, noise, and phase ambiguity in PnO calculations, as described in U.S. Pat. No. 10,234,306. For example, assume Sigmat is being distorted by a nearly uniform EM field generated by a large wire loop on the floor. To model distortion, the direction of the distortion field (v) and the gains per frequency (P) may be determined.

The Distortion field: $E(r) = v \cdot P$ v—3×1 direction of the distortion field (same for all three frequencies)

P—1×3 gains for the distortion field per frequency (scalar)

$$X = N^t(B(r) + v \cdot P) \qquad \text{Equation 3}$$

Position and orientation may also be corrected by a gravity equation derived from a fusion of the IMU's accelerometer and gyroscope by means of a Kalman filter sensor fusion, as detailed in U.S. Patent Application 2016/0377451A1.

$$N \cdot G_{rx} = G_{tx} \qquad \text{Gravity equation:}$$

A portion of the gravity equation can be substituted for direction of the distortion field ("v"). This substitution simplifies the distortion field to the roll about gravity, which reduces the number of unknown variables and makes the equation more easily solved. The equation is easier to solve because it reduces the degrees of freedom (DOF) of N (orientation) from 3 angles to just 1 (roll about gravity). See U.S. Pat. No. 10,162,177 for more information. Substituting the direction of the distortion field ("v") in equation 3 with Grx yields equation 4:

$$X = N^t B(r) + G_{rx} \cdot P \qquad \text{Equation 4}$$

7 parameters must be determined to solve equation 4:
θ—roll angle of N
r—3D position vector
P—distortion gains The Sigmat has 9 values (9>7) so a unique solution is probable. Solving the equation analytically is difficult, however iterative optimization methods offer a simpler solution through the use of a Jacobian. (e.g. Levenberg-Marquardt algorithm).

(SOLVER 1):

$$F(\theta, r, P) = \|N(\theta) t B(r) + Grx \cdot P - X\|^2 \qquad \text{Equation 5}$$

First, (θ, r) are initialized using an analytic dipole solution (ignoring distortion) or by tracking, initialize P=(0,0,0). Next, the Jacobian of F(θ, r, P) is computed using numerical derivatives. The Jacobian is used to compute a step which decreases F. A final calculation step is to perform iterations until some tolerance is achieved. The value of corrected PnO is then compared to measured PnO to determine the ratio of unexplained Sigmat and confidence intervals. Equation 6 is used for blending the three solvers.

$$E_x = (\|X_{PnO} - X_{Measured}\|)/(\|X_{measured}\|) \qquad \text{Equation 6}$$

When EM+IMU fusion provides the constraint, the equation becomes:

(SOLVER 2):

$$X = N_f B(r) + v \cdot P \qquad \text{Equation 7}$$

Where N=Nfusion

Electromagnetic and Optical Coordinate System Merger

In some embodiments, the electromagnetic tracking system is self-referential, where PnO is established relative to a wearable transmitter with unknown global coordinates. A self-referential tracking system can be merged with a global coordinates system in many ways. In one example, the present disclosure provides a system including a camera 204. The camera 204 records and analyses images of the player's surroundings to establish an anchor point (e.g. a (0, 0, 0) point). The movement of this camera 204 is calculated as movements relative to this global coordinate anchor point.

Systems and methods of the present disclosure typically include a sensor 202A configured to enable the tracking system's translation from self-referential coordinates to global coordinates. Such a sensor 202A has a fixed position relative to the system's cameras 204. This fixed position provides a known distance and orientation between the self-referential coordinates and the global coordinate, allowing their merger, as described in U.S. Pat. No. 10,162,177.

When merged, the benefits of both coordinate systems are maximized while the downsides are minimized. Anchoring a tracking system in real space and accurately positioning the player, as a whole, in VR may be best achieved by an optical system. However, an optical system is limited by line of sight and is therefore not ideal for determining player positional nuances, such as limb location and other body configuration information. On the other hand, an electromagnetic system is excellent at tracking limb position and body configuration, but typically requires a stationary transmitter for position tracking relative to a real-world reference. By combining the two systems, the entire system of sensors may be optimized to be both mobile and accurate.

Processor(s)

Systems and methods of the present disclosure use one or more processors that execute a number of instructions, such as machine-readable instructions. The instructions include receiving, storing, processing, and transmitting tracking data from EM, optical, IR, IMU, and/or myoelectric sources. The tracking data may be communicated to the processor by either a wired or wireless communication link. Upon receiving tracking data, the processor may execute an instruction to permanently or temporarily store the tracking data as random access memory (RAM), read only memory (ROM), cache, flash memory, hard disk, or other suitable storage component. Such a memory component may be a separate component in communication with the processor, or may be integrated into the processor.

The processor may also execute instructions for constructing an instance of virtual space. The instance may be hosted on an external server and may persist and undergo changes even when a user is not logged into said instance. Alternatively, the instance may be user specific and the data required to construct it may be stored locally. In such an embodiment, new instance data may be distributed as updates that users download from an external source into local memory. In either embodiment, the instance of virtual space may include a virtual volume of space, a virtual topography (e.g. ground, mountains, lakes), virtual objects, and virtual characters (e.g. non-player characters "NPCs"). The instance may be constructed and/or rendered in 2-D or 3D. The rendering may offer the user a first person or third person perspective. The instance may include properties of physics, such as gravity, magnetism, mass, force, velocity, and acceleration, that cause the virtual objects in the virtual space to behave in a manner at least visually similar to real objects in real space.

The processor may execute a program for analyzing and modeling tracking data. For instance, the processor may execute a program that analyzes the tracking data it receives according to the equations described above, along with other related pertinent mathematical formulas. Such a program may incorporate a graphics processing unit (GPU) that is capable of translating tracking data into 3D models. The GPU may utilize mesh puppetry, a skeleton rig, vertex animation, a shader engine, an inverse kinematic (IK) engine, and/or similar animation tools. In some instances, the CPU may at least partially assist the GPU in making such calculations. This allows the GPU to dedicate more resources to the task of converting 3D scene data to the projected render buffer. The GPU may refine the 3D model by using one or more algorithms, such as an algorithm learned on biomechanical movements, a cascading algorithm that converges on a solution by parsing and incrementally considering several sources of tracking data, an inverse kinematics engine, a proportionality algorithm, and other algorithms related to data processing and animation techniques. After the GPU constructs a suitable 3D model, the processor executes a program to transmit data for the 3D model to another component of the computing environment, or to a peripheral component in communication with computing environment, that is capable of displaying the model. In some embodiments, the GPU transfer the 3D model to a video encoder or a video codec via a bus, which then transfers information representative of the 3D model to a suitable display. The 3D model may be representative of a virtual entity that can be displayed in an instance of virtual space, e.g. an avatar. The virtual entity is capable of interacting with the virtual topography, virtual objects, and virtual characters within virtual space. The virtual entity is controlled by a user's movements.

FIG. 3 illustrates an example of an animation pipeline for rendering an avatar. The animation pipeline starts by collecting tracking data from sensors 202 worn by a player 303. This tracking data is collected and processed to form a 3D model 304 of the player's body. The collection of the data may be achieved by the HMD 201 and the data may be processed by a processor, a GPU, or some combination thereof. The 3D model 304 may be comprised of virtual bones, and a virtual skin or mesh as discussed in more detail below. Once a proper 3D model 304 is determined for the player's latest movements, a surface of the model is animated as an avatar 305 in the virtual reality environment for the player to see and control. Fast execution of this pipeline may be important t so that there is a minimal delay between collecting tracking data and animating the avatar exhibiting tracked movements in the virtual reality environment. A delay between a player's movements and their avatar's movements may diminish the player's sense of immersion in VR. In some embodiments, the avatar is animated without a head. A person typically cannot see their head, so this may typically not be an issue. In some embodiments, the virtual reality environment may include a mirror or mirrored surfaces. In such instances, the avatar may be animated with digital rendering of the player's face, which may show up in the mirrors and mirrored surface.

In some embodiments, a processor may execute instructions for a supervised learning algorithm that predicts position and orientation when tracking data is limited or unreliable. The algorithm is trained to weight different prediction techniques based on the type and amount of available tracking data. The algorithm may be trained to predict anthropomorphic movements with a forward and backward reaching inverse kinematics ("FABRIK") engine, to identify and replicate repetitive movements with a frame-by-frame analysis, and to match prior positions and partial tracking data with positions in a key pose library. In some examples, the algorithm will weight FABRIK solvers as more reliable when tracking data for an end effector is available. In some examples, the algorithm will weight a frame-by-frame prediction or matching prediction as more reliable when tracking data for an end effector is lacking.

The algorithm may utilize a FABRIK solver to predict position and orientation when tracking data is lacking. A FABRIK solver uses a two-bone inverse kinematic chain to determine movements of a skeleton that reposition an end effector to a new, tracked location. The joints of the skeleton may be restricted to only allow anatomically correct movements relative to a known end effector location. This may be achieved by restricting joint mobility. Translational movement may be restricted with a bounding box and rotational movement may be restricted to a maximal anatomically possible range of motion. Similarly, the degrees of freedom of any joint may be limited to six degrees of freedom or less. If tracking data for an end effector is lacking, the algorithm may weight FABRIK solver solutions lower and may rely more heavily on other prediction methods.

A learning algorithm may be trained to predict position and orientation patterns by analyzing tracking data frame-by-frame and applying a smoothing function. The term learning algorithm or machine learning may generally refer to any system or analytical and/or statistical procedure that may progressively improve computer performance of a task. Machine learning may include a machine learning algorithm. The machine learning algorithm may be a trained algorithm. Machine learning (ML) may comprise one or more supervised, semi-supervised, or unsupervised machine learning techniques. For example, an ML algorithm may be a trained algorithm that is trained through supervised learning (e.g., various parameters are determined as weights or scaling factors). ML may comprise one or more of regression analysis, regularization, classification, dimensionality reduction, ensemble learning, meta learning, association rule learning, cluster analysis, anomaly detection, deep learning, or ultra-deep learning. ML may comprise, but is not limited to: k-means, k-means clustering, k-nearest neighbors, learning vector quantization, linear regression, non-linear regression, least squares regression, partial least squares regression, logistic regression, stepwise regression, multivariate adaptive regression splines, ridge regression, principle component regression, least absolute shrinkage and selection operation, least angle regression, canonical correlation analysis, factor analysis, independent component analysis, linear discriminant analysis, multidimensional scaling, non-negative matrix factorization, principal components analysis, principal coordinates analysis, projection pursuit, Sammon mapping, t-distributed stochastic neighbor embedding, AdaBoosting, boosting, gradient boosting, bootstrap aggregation, ensemble averaging, decision trees, conditional decision trees, boosted decision trees, gradient boosted decision trees, random forests, stacked generalization, Bayesian networks, Bayesian belief networks, naïve Bayes, Gaussian naïve Bayes, multinomial naïve Bayes, hidden Markov models, hierarchical hidden Markov models, support vector machines, encoders, decoders, auto-encoders, stacked auto-encoders, perceptrons, multi-layer perceptrons, artificial neural networks, feedforward neural networks, convolutional neural networks, recurrent neural networks, long short-term memory, deep belief networks, deep Boltzmann machines, deep convolutional neural networks, deep recurrent neural networks, or generative adversarial networks.

Figure 4:
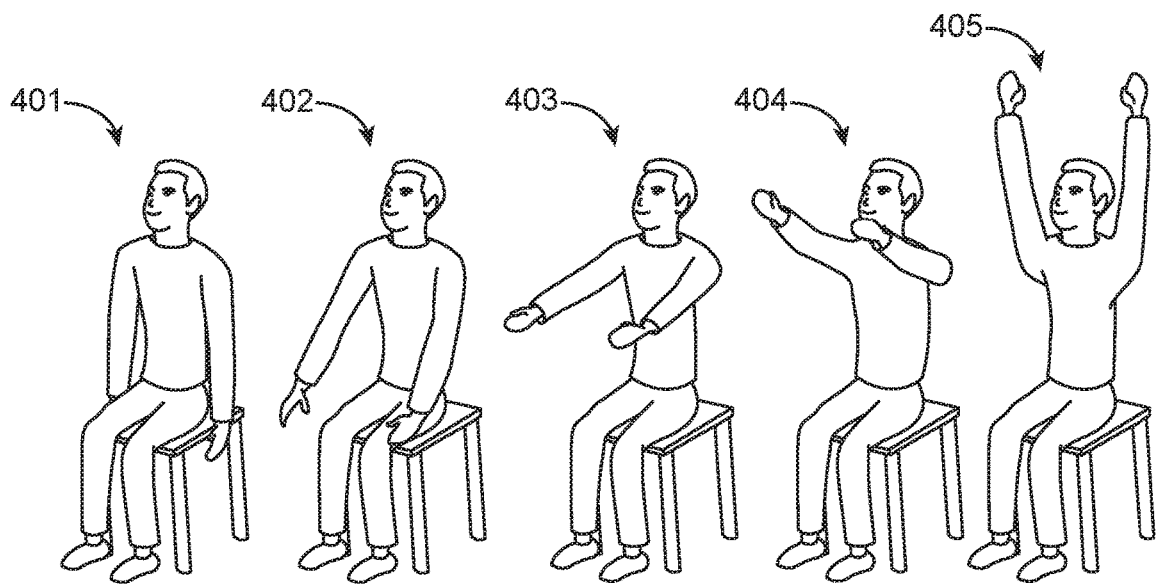
FIG. 4 illustrates an example tracking data cluster, in accordance with some embodiments.

In one example, the algorithm receives a first level of training data comprised of tracking data of a person performing a repetitive exercise, such as that depicted in FIG. 4. The training data set is purpose built to include a frame or series of frames where tracking data is at least partially missing. The algorithm is tasked with predicting the person's complete position and orientation for the missing frames. In one example, the algorithm identifies frames with complete tracking data on either side of the missing frame or series of missing frames, i.e. the adjacent frames. The algorithm then executes a smoothing function that animates a blend space between the adjacent frames that results in a smooth and continuous motion. The smoothing function incrementally blends the values of two adjacent frames, so the first input gradually transforms into the second input. For instance, if the first input is position 402 of FIG. 4 and the second input is position 404, the position 403 may be one of the blend space renderings the algorithm animates between positions 402 and 404. The algorithm may further analyze prior tracking data to identify clusters of tracking data that exhibit repetitive position and orientations and identify where in the cluster the most recent frames belong. If the partial tracking data and prior frames can be matched to a cluster where tracking data is complete, the algorithm may simply replicate the prior frame(s) in that cluster. In some instances, the smoothing function identifies a cluster with some but not all of the missing frames and the smoothing function uses this cluster to serves as intermediary blend space inputs between adjacent frames, which typically increases accuracy.

In a second example, the algorithm receives a first level of training where, the algorithm is provided with a complete series of tracking data for a repetitive exercise and is tasked with applying a smoothing function for gaps in the data that produces a finished series of tracking data with no gaps and smooth and continuous exercise movements. For a second level of training in this example, the algorithm is provided with a series of tracking data where the last frame is missing at least some of the tracking data. The algorithm is then tasked with predicting in near live time (e.g. faster than $\frac{1}{60}^{th}$ of a second) the complete tracking data for the last frame by identifying patterns in movement in the series of tracking data, wherein the algorithm identifies clusters of frames with repetitive movements and assumes continued adherence to the repetitive motion for the last frame.

FIG. 4 illustrates a cluster of frames an algorithm has identified within a series of tracking data. The algorithm identified this cluster because the series of tracking data shows similar movements to this cluster over and over. The algorithm has identified a pattern in the series of tracking data of movements from position 401, to 402, to 403, to 404, to 405, to 404, to 403, to 402, to 401. After the algorithm has identified a cluster, it may then predict one or more missing frames by assuming adherence to the cluster's pattern. For instance, assume the algorithm has an adjacent frame 402, then has two missing frames, and then another adjacent frame 405. The algorithm may predict that the proper frames to animate for the missing frames are something similar to positions 403 and 404. In some examples, the algorithm has identified this cluster and then has a last, most recent missing frame it may predict in near live time. The algorithm examines the two most recent frames as being similar to positions 402 and 403, and in that order, the algorithm then predicts that the next frame may look like position 404 from the cluster and animates that position to provide a smooth animation for this frame where tracking data was temporarily lacking. It should be appreciated that FIG. 4 is only illustrative of some positions within a cluster. Assuming the back and forth movements of FIG. 4 take 10 seconds for each repetition, and assuming tracking data is collected 60 times per second, the cluster represented by FIG. 4 would actually include 600 frames for the algorithm to reference when tasked with providing a smoothing function.

In some examples, the algorithm is provided with a second level of training data comprised of a series of frames where tracking data is lacking across one or more most recent frames, and the algorithm is tasked with predicting these most recent frames. For instance, the algorithm is provided with information of the previously rendered body position, the series of all past body positions, and limited tracking data for the current body position. The algorithm may identify patterns in available tracking data to find a cluster of frames that are repeated, e.g. a cluster function. The algorithm may identify where in the cluster the most recent frames have improved fit between the tracking data and one or more frames of the cluster. The algorithm then renders the most recent frame(s) as following the same patterns as identified in the cluster. The cluster function prediction is particularly effective when tracking a player performing an exercise with repetitive movements. When tracking data is temporarily lacking, the algorithm may simply assume continued adherence to the pattern of movement and render a next frame of movement that is continuous with the player's pattern of movement.

In one example of a third level of training, the algorithm is provided with a set of training data that is restricted across some joint, so movement information beyond the joint may be predicted based on the movements of adjacent body parts alone. In other words, the tracking data lacks an end effector and position and orientation may be predicted based on a cluster function or a key pose match. For instance, tracking data for fingers may be categorically unavailable or temporarily lacking. The position of the fingers may be rendered according to matches in a library of key poses, wherein the match is based on position, orientation, directionality, and velocity of hand, metacarpus, wrist, or arm movement alone.

In some examples of a third level of training, the learning algorithm may be trained to predict position and orientation by consulting a library of key poses. A key pose library may be filled with tracking data for common position and orientations a player finds themselves in when performing exercises. In one example, the available tracking data is compared to the key pose library. The available tracking data may include past frames of complete tracking data and one or more recent frames of partial tracking data. This available tracking data is compared to individual key poses and to blend spaces between two or more key poses to search for strong matches. The algorithm may reject matches between partial tracking data and a given key pose if rendering the key pose would result in a jerk or teleportation. For instance, if the tracking data at time 0 was complete and at time 1 was lacking arm position, the algorithm may compare the partial data to key poses. The algorithm may then reject a key pose with a perfect match to the partial data of time 1 if the arm position of the key poses is not close in position and orientation to the arm position of time 0. Only a small amount of movement may be allowed from frame to frame (typically 60 frames are animated per second) to ensure smooth and continuous animations. The algorithm may further utilize a cluster function to identify patterns and match key poses in sync with the cluster's pattern and render the missing data accordingly. The strength of a match may be improved with a weighting function that weighs joints close to the missing data more than joints and body parts distant from the missing data when assessing strength of a match with a key pose. In some instances, individual key poses may have an associated directionality, a velocity vector transformation function, or both. For instance, tracking data indicating a hug position may render the fingers as curling in when advancing towards the hug, while the fingers splay out when retracting from the hug. In this way, a single key poses may have two or more associated hand positions dependent on directionality. Furthermore, the degree to which the fingers curl in or stretch out may be proportional to the speed at which the arms are moving. The algorithms discussed here are typically supplied with a large amount of training data sets. After the algorithm provides an output for each training data set, the output is compared to the correct output and the nodes of the algorithm are reweighted according to their contribution to the correct or incorrect output.

In some embodiments, a processor may execute instructions for a cascading algorithm that converges on a solution by parsing available data and analyzing the parsed data incrementally. For instance, the cascading algorithm may utilize EM tracking data, camera tracking data, IMU tracking data, proportionality parameters, and constraint parameters. Convergence is achieved, in one example, by assessing the last 3D model and defining constraint parameters for maximal movement across each joint in the given time frame. The algorithm then searches the EM tracking data for a solution satisfying that constraint. This solution is compared to available IMU tracking data and modified accordingly. The algorithm then takes that solution and refines it according to proportionality parameters that define appropriate angle, lengths, and distance between various body parts. Refinement may be achieved using least squares, standard deviations, an average, or a median method and may disregard data that significantly deviates from the rest (e.g. outliers). If available, the algorithm then consults camera tracking to verify that the solution accurately represents the user's movements and body position as captured by the camera(s). The algorithm may repeat one or more of these steps to reach convergence on an acceptable solution and the algorithm may temporarily, permanently, or continually modify the order in which the steps are executed to reach convergence more quickly. Convergence is achieved when the algorithm achieves an acceptable degree of confidence that the correct solution has been identified. For some portions of the avatar, where accuracy is not absolutely crucial, this confidence level may be lower, such as leg position when seated. For other portions, this confidence level may be higher, such as hand position and orientation. The animation of high priority body parts may receive processing prioritization to ensure animations do not exhibit visible latency. Animation prioritization may be achieved through streamlining the animation pipeline in software, hardware, or a combination of both, as described in U.S. Pat. No. 8,520,010.

Visual Display

In some embodiments, the computing environment generates a 3D model of the user, an instance of virtual space, and then communicates that information for display. An audio and visual display may be in communicable connection with computing environment by a head mounted display (HMD) 201, as typical in VR systems, a television, a high-definition television, a monitor, or the like. The audio and visual display may be visualized on a cathode ray tube (CRT) display, light-emitting diode display (LED), plasma display panel (PDP), organic light-emitting diode (OLED) display, liquid crystal display (LCD), electroluminescent display (ELD), and other visualization hardware. In some embodiments, a user's movements in physical space are mapped onto a 3D model 304 and at least a portion of that model is rendered in virtual reality, which the user can see and control (e.g. an avatar 305). In some embodiments, the displays of the virtual 3-D model are replicated on a physical 3D model, such as a prosthetic limb.

Example HMDs include but are not limited to Oculus Rift, Oculus Go, Oculus Quest, HTC Vive, Valve Index, PlayStation VR, Razer OSVR, Fove VR, StarBreeze StarVR, Pimax, VRgnineers VRHero, VRgnineers XTAL, Deepoon VR, Dell Visor, Asus HC, Acer WMR, HP WMR, HP Reverb, Lenovo Explorer, Samsung Odyssey Samsung Gear VR, Varjo VR, LG Steam VR, GameFace Labs, HELMET VISION, Avegan Glyph, Microsoft Hololens, Pico VR Goblin, Pico VR Neo, Qualcomm Snapdragon, Alcatel Vision, Woxter Neo, Lenovo Mirage, Google Daydream, etc.

Example System

In general, the computing environment utilizes PCBs with sensors, processors, GPUs, and other peripheral computer components to collect tracking data, map tracked movements onto an avatar, display at least a portion of the avatar for a user, and display a virtual reality environment.

In a more specific embodiment, systems and methods of the present disclosure utilize a tracking system comprised of multiple, independent PCBs, a head mounted display (HMD) 201, and a camera 204 to wirelessly track user movement accurately and precisely. Each PCB typically supports an electromagnetic (EM) sensor 202, which may be comprised of an EM receiver and an EM emitter/transmitter. The HMD 201 typically houses the camera 204, an EM sensor 202A at a fixed distance from the camera 204, and a visual display for viewing virtual reality. The HMD 201 may also act as the host of the tracking system by including a processor and graphics processing unit (GPU) configured to track the movements of the user, generate an avatar representing the user, and generate a virtual reality environment. In total, eleven or more electromagnetic sensors may track body position and orientation.

Figure 5:
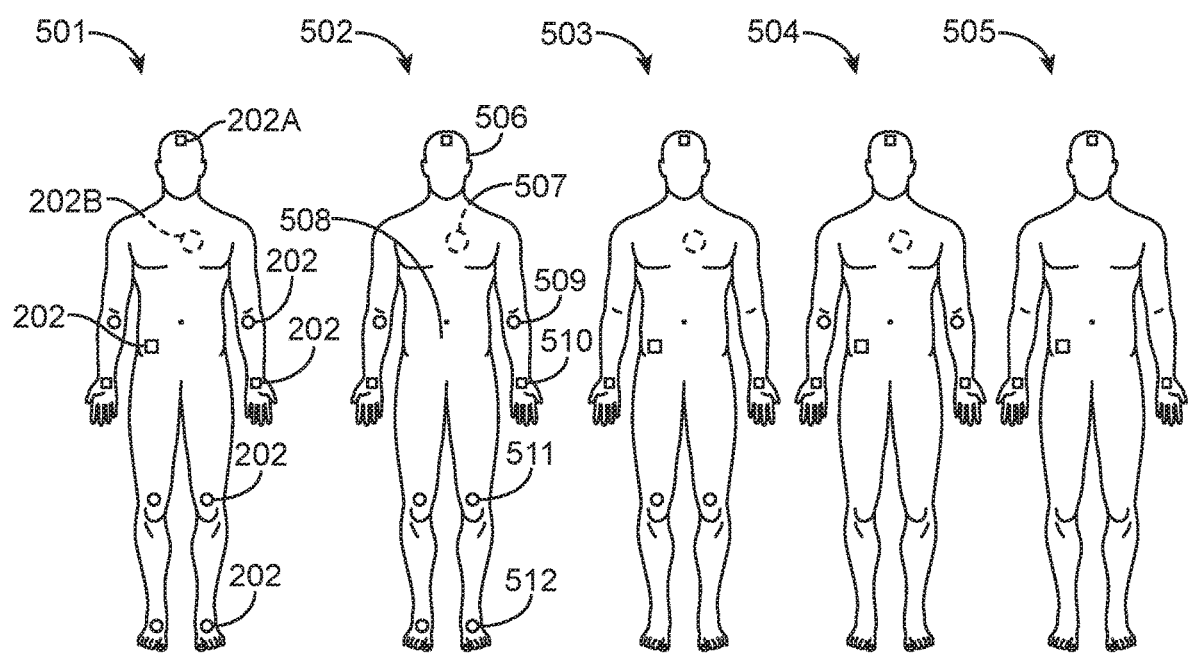
FIG. 5 schematically illustrates different sensor positions on a user's body, in accordance with some embodiments.

FIG. 3 illustrates an example of a user 303 fitted various sensors configured to capture, analyze, and track the user's 303 movements. In one example, a user 303 is fitted with an HMD 201 and cloth straps 205 are used to attach numerous sensors 202 containing an EM receiver, an EM emitter, or both on the wrists, elbows, waist, and on back, collectively, the "modules." In some embodiments, the system also includes sensors on the knees and ankles as depicted in FIG. 5. The system may comprise any number of modules for example, the number of modules may be less than 10,000, less than 100, less than 50, less than 20, less than 10, etc. Systems and methods of the present disclosure may include more sensors. For example, a system may include 10, 20, 50, 100, 200, 500, 1000, 10000 sensors or more.

Orchestration

In some embodiments, the HMD 201 may act as a host that orchestrates the operation of the various modules and acts as the conduit between the various modules. In one example, the host sends upstream information via radio frequency (RF) to other modules. Upstream information may include frequency shift, LED color shift, auto-syncing guidance, and other various commands. In this example, the various modules send downstream information via RF to the host, such as sync status and calculated PnO.

Auto Sync Protocol

In some embodiments, each of the wearable sensors are initially unassigned. In some embodiments, upon startup and placement, the sensors may begin to auto-sync. Auto-body-positioning allows for seamless, error-proof setup, and requires no manual input. Once the sensors are placed on the body, the system automatically determines where on the body each sensor has been placed and assigns them as such. This auto-syncing feature improves on ease of use by simplifying and expediting the process of starting the system. In one example, the sensors 202 placed on the body provide PnO data relative to a sensor 202B with an emitter worn on a user's back. The PnO data is then analyzed by the host to determine the positioning of the various sensors. Two variables can be used to determine the location of every sensor, height and hemisphere (e.g. right or left side). In the example of the user 303 in FIG. 3, the sensor with the highest position is easily identified as the sensor 202A on the HMD 201. The sensors 202 having a height closest to the emitter sensor 202B worn on the back are assigned as the left and right elbows, respectively. Moving down, three sensors 202 are positioned at about waist height. A middle-most sensor at this height is assigned as the waist sensor, and the left sensor is assigned as the left wrist and the right sensor is assigned as the right wrist. The knee and ankle sensors may be similarly identified by their hemisphere (left or right) and their height. Although the variable height and hemisphere were used in the example above, this should be understood as a simplification of one way to achieve auto-syncing. For instance, the magnetic field vectors received at each sensor must be processed before they can determine height and hemisphere. The magnetic field vectors may alternatively be processed to determine absolute distance from an emitter. Additionally, if the player moves his or her arms, accelerometers inside the sensors may help identify the wrist and elbow sensors. During arm movements, typically the wrists will have the greatest acceleration of all the sensors, and the elbows may an acceleration lower than the wrists and higher than the other sensors. The rest of the sensors may then be determined by height alone. Systems of the present disclosure may use other such processing methods or combinations of such methods, to determine relative sensor location.

Limited Movement Data in Body Tracking

Even when employing state of the art tracking techniques, tracking data on a given body part may be temporarily inadequate from time to time. At least one problem in VR systems may be the challenge of animating an avatar when tracking data for a portion of the user or subject's body is permanently or temporarily unavailable. For example, a limited number of sensors may be disposed on a body of a user or a subject and an avatar may be animated to include non-tracked body parts. For example, a forearm may be tracked but the motion of the hand or the wrist or the fingers may not be tracked. For example, a body part may be tracked but the sensor may temporarily not be transmitting data (e.g. line of sight to a receiver may be blocked).

FIG. 5 illustrates potential sensor 202 placement options. In a first example 501, the sensors 202 are attached to the head 506, the back 507, the waist 508, the elbows 509, the wrists 510, the knees 511, and the ankles 512 for a total of eleven sensors tracking player movement. The sensor placement of this example 501 is optimal for accurately tracking the movements of an entire body. In other embodiments, some but not all of these sensors are attached to a player. In a second example 502, the sensors 202 are attached to the head 506, the back 507, the elbows 509, the wrists 510, the knees 511, and the ankles 512 for a total of ten sensors. In a third example 503, the sensors 202 are attached to the head 506, the back 507, the waist 508, the wrists 510, and the knees 511, for a total of seven sensors. The sensor placement of this example 503 enables nearly full body tracking with untracked movements of the elbows and feet being predicted and animated based on the movements of tracked body parts. In a fourth example 504, the sensors 202 are attached to the head 506, the back 507, the waist 508, the elbows 509, and the wrists 510, for a total of seven sensors. This setup may offer improved tracking of the upper body and is useful for tracking exercises performed while sitting. In a fifth example 505, the sensors 202 are attached to the head 506, the waist 508, and the wrists 510, for a total of four sensors. This setup may track arm and spine movements well. Typically, sensors are attached to at least the wrists for exercises requiring arm movement, the waist sensor for exercises requiring leaning, and the ankles for exercises requiring leg movement. In any of the forgoing embodiments, cameras mounted on the player may assist in tracking.

In each of these embodiments, tracking information for some body parts may be completely or be temporarily unavailable. For instance, the fingers may not directly be tracked and camera tracking may suffer from line of sight challenges, distance issues, and computational limitations. Elbow and leg position may not be tracked and camera tracking may suffer from line of sight or distance issues. Feet and toe positions are not tracked, and shoes may eliminate the possibility of camera tracking. In essence, these tracking systems provide limited data from which to determine the position and movements of an entire avatar.

Systems and methods of the present disclosure fill at least some informational gaps in tracking technology by generating animations for body parts where tracking is categorically unavailable, where tracking is temporarily lacking, or to merely refine tracking based animations. A least one goal is to provide a full avatar with accurate and life-like biometric movements even with limited movement data to ensure maximal spatial immersion for the user.

Limited Data to Support Hand and Finger Animations

In some embodiments, systems and methods of the present disclosure collect tracking data from or near a player's wrist or metacarpus, generates complementary finger movements, and displays both. Relaxed fingers tend to move as a person moves their wrist. The fingers automatically curve, bend, and splay as the wrist bends, supinates, and pronates. From this observation, the orientation of a player's fingers can be predicted based on the orientation of the player's hand, wrist, or metacarpus. This is an example of an animation solution that transcends joints without an end effector (i.e. tracking data on one side of an articulating joint is used to determine movements on the other side of the joint).

Figure 6A:
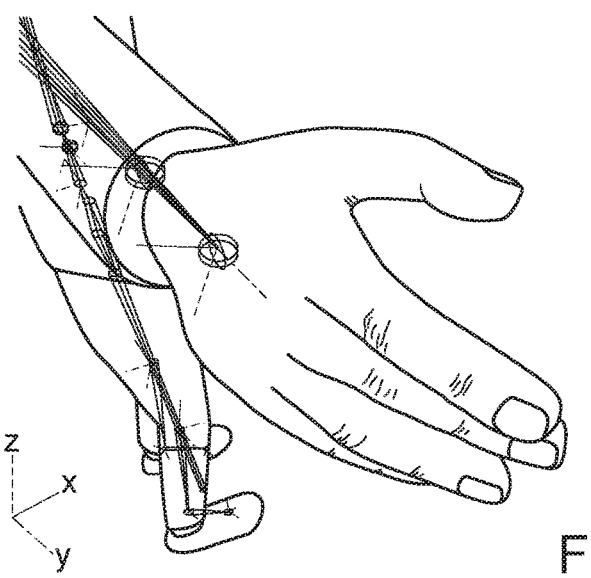
FIGS. 6A-6E illustrate examples of tracking a user's metacarpus movement to impute finger movement, in accordance with some embodiments.
Figure 6B:
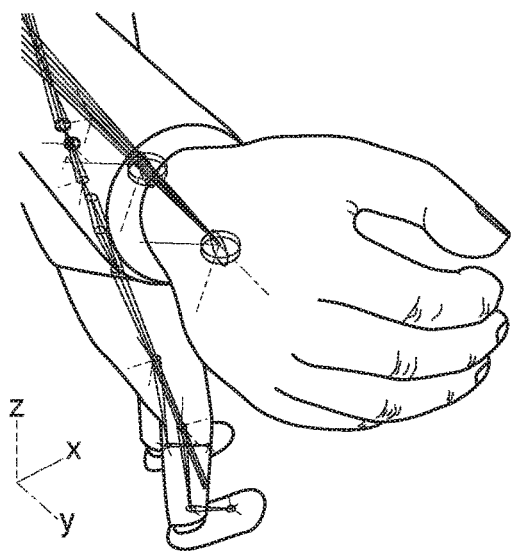
Figure 6C:
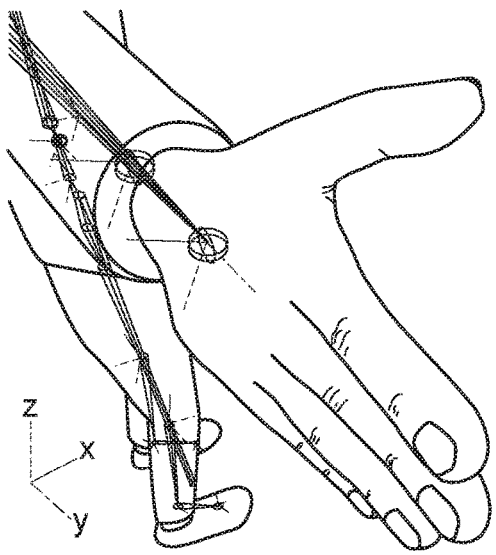
Figure 6D:
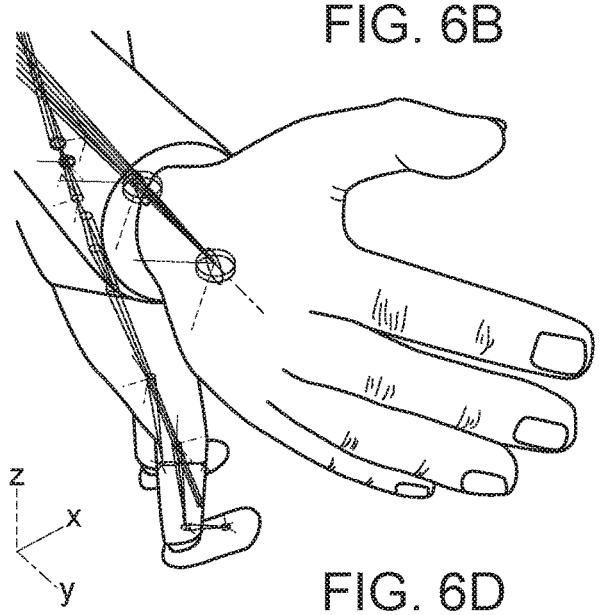
Figure 6E:
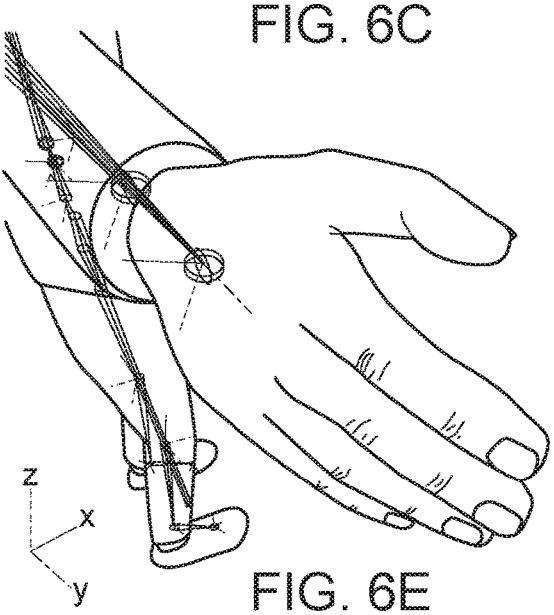

FIGS. 6A-6E illustrate various examples of finger position animations that may be rendered based on hand, metacarpus, or wrist movements alone. FIG. 6A illustrates a hand with the thumb pointing upwards and fingers sticking out with a small curve towards the palm, hereinafter the "neutral" position. From this frame of reference, "in" refers to the wrist bending the palm towards the forearm (FIG. 6B), "out" refers to the wrist bending the back of the hand towards the forearm (FIG. 6C), "up" refers to the wrist bending the thumb towards the forearm (FIG. 6D), and "down" refers to the wrist bending the pinky towards the forearm (FIG. 6E).

When a player's wrist is tracked as moving in, the avatar's hands may curl towards the palm, as depicted in FIG. 6B. In alternate embodiments, as a player's wrist is tracked as moving in, the avatar's hands curl with the pinky curling the first and curling the furthest in, while the ring finger, middle finger, and index finger curl sequentially, whereby each finger curls to a slightly lesser extent than the last. As a player's wrist is tracked as moving out, the avatar's hands may straighten, fingers may bend slightly backwards, and some fingers may splay outwards relatively evenly, as depicted in FIG. 6C. As the player's wrist is tracked as moving up, the avatar's thumb may reach towards the forearm, the fingers may slightly splay, the fingers may gently curve towards the palm, and the pinky may crunch in, as depicted in FIG. 6D. As the player's wrist is tracked as moving down, the avatar's pinky may reach towards the forearm, the fingers may splay, the fingers may straighten, and the fingers may bend backwards, as depicted in FIG. 6E.

Limited Data Across Elbow, Knee, Feet, and Toe Tracking

At a given instance, the tracking data for a portion of a player's body may be permanently or temporarily limited. A tracking system may not track a player's elbows or the tracking system may attempt to track a player's elbows and then, at least temporarily, fail to provide accurate tracking data. Systems and methods of the present disclosure step in when tracking data for the elbow is absent or inaccurate. The tracking data from adjacent body parts, such as the hands and/or head, are used to determine possible elbow locations. In some embodiments, an inverse kinematics engine utilizes hand positions as an end effector to determine elbow location. In an alternative embodiment, the location of the head and hands physically constrains the possible locations of the corresponding elbow. Typically, the elbow is located between the head and hands. Elbow position is constrained to be within a forearms length of the tracked hand, which can be used to create a spherical surface of possible solutions. Elbow position is also constrained in relation to the head, the elbow is biomechanically limited to a range of positions relative to the head. This range of positions is compared to the prior determined spherical surface of possible solutions, and areas of overlap are possible solutions. These possible solutions are compared to prior solutions—i.e. tracking over time—to help pin down the proper angle for the joint based on earlier movement data. In some embodiments, available tracking data is processed by a neural network trained on biomechanics, as discussed above. The system then generates an expected elbow location. Absent conflicting information (such as tracking data on elbow position), an elbow is animated in the expected location. If there is conflicting location information, the system may disregard conflicts that propose drastically different locations and the system may normalize between the expected location and the conflicting data when the two positions are close in space. Such techniques may be used to determine finger positions as well.

A tracking system may permanently or temporarily lack accurate tracking data from a player's knees and feet. In some embodiments, systems and methods of the present disclosure consult tracking data from the head, hands, waist, and/or legs to predict the movements of the player's knees and feet. The system applies the same techniques for determining elbow position for determining the position of the knees and feet. For example, waist tracking data can be used to establish a range of possible positions for the knees and feet. Furthermore, cameras and IMUs may indicate the waist's distance from the ground. Combining this information with the user's leg length allows the system to further constrain the range of possible positions for the knees and feet.

In one application, the user's height and the waist sensor's distance from the ground indicate that the user is likely seated. Alternatively, the user is playing a game where being seated is presumed. In either case, the system uses at least the waist sensor to determine the possible location of the knees and feet. For instance, in a neutral seated posture the knees and feet may be presumed to be about one foot apart and orientated vertically. As the waist is tracked as moving forward, the knees may be animated to widen and the soles of the feet may be animated rise on their outer edges. Alternatively, the knees may narrow and the feet may rise on their inner edges. Which variation happens may depend on settings and/or hand tracking data. For instance, a hand tracked as reaching below the waist at or near the body's midline may cause an animation of the knees to widen. While a hand tracked as reaching below the waist near the body's sideline may cause an animation of the knees to narrow. In further embodiments, tracking data indicative of the waist leaning to the right or leaning to the left may cause the knees to be animated as leaning to the right and to the left, respectively. (e.g. the torso lean is mimicked in the knees and feet). Such animations may be verified against camera tracking data that may occasionally capture leg image data.

In some embodiments, systems and methods of the present disclosure animate toe movements on an avatar. Optical tracking and wearable tracking devices for the toes are largely impractical or ineffective. The most practical approach for animating toe movement is to track adjacent joints, such as the ankles, knees, hips, and/or waist and from this tracking data predict the most probable movements of the toes. Like the fingers, when a foot bends and twists at the ankle, the toes move in a predictable manner. In some embodiments, systems and methods of the present disclosure provide animations for the toes that are complementary to the movements at these other joints. For instance, tracking data indicative of a user raising the balls of their feet, while keeping the heel planted, may cause the animation of stretching and/or splaying toes. Tracking data indicative of ankle rotation may cause animations reaching in the same direction of said rotation. Tracking data indicative of a user standing on their tip toes may cause animations of the toes flexing to grip the ground.

Data to Support Amputated Limb Tracking

Figure 7:
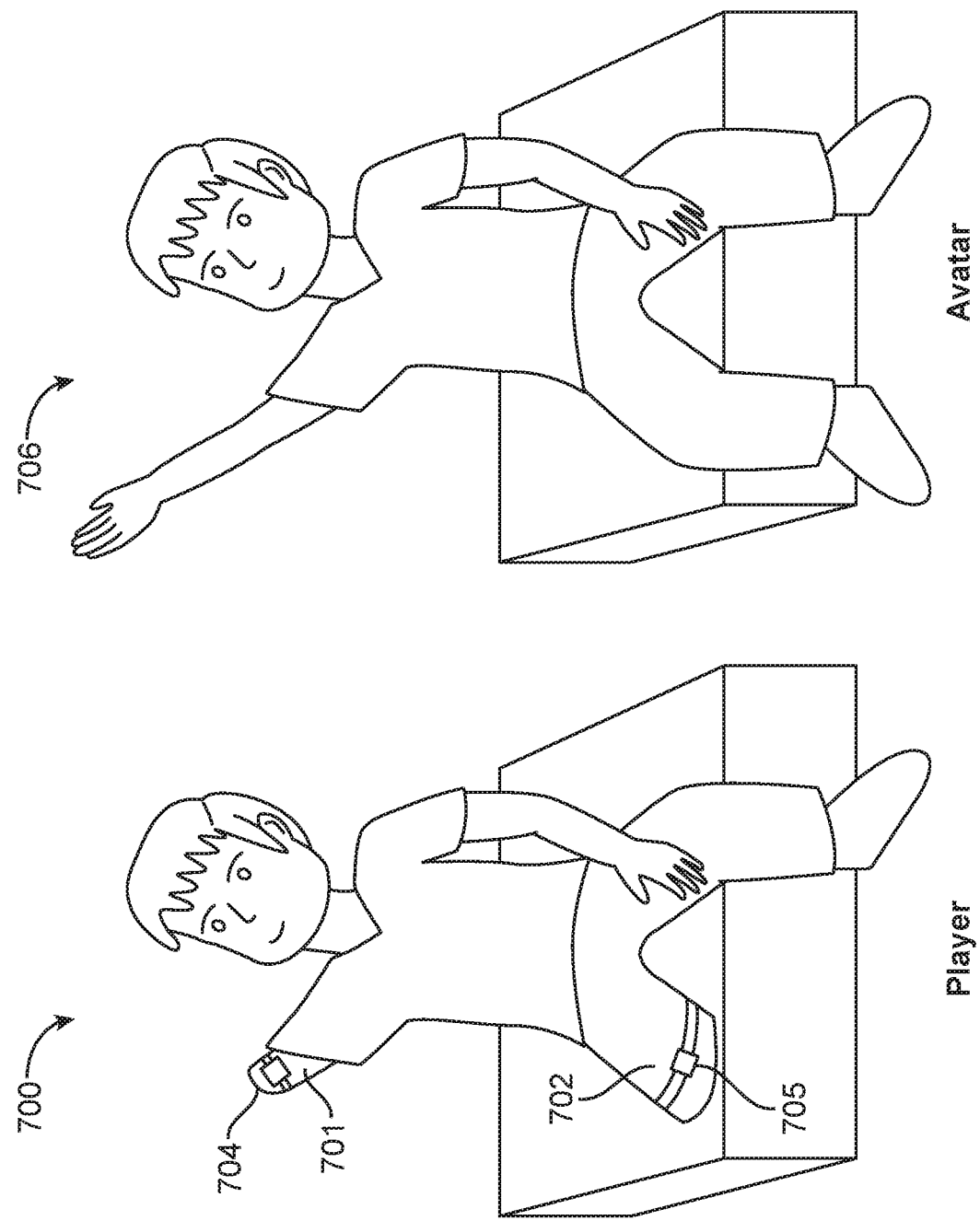
FIG. 7 provides an example of how limited data can be used to track an amputated limb, in accordance with some embodiments.

FIG. 7 illustrates generation of full bodied avatars 706 for users 700 with one or more missing limbs, in accordance with some embodiments. Body parts around an amputated limb 701, 702 may be tracked for movement. This movement information may then be used to generate an avatar 703 having the missing limb, whereby the "phantom limb" exhibits complementary movements to the player's tracked movements. The most probable movements are optionally determined by a learned algorithm trained on biomechanics, as discussed above. The algorithm determines the most probable movements based on available tracking data. Optionally, myoelectric tracking is employed. Myoelectric tracking tracks and records EMG signals at or near the stump (e.g. 704, 705) to determine intended movements. Intended movements are then considered in the determination of the most probable movements. However, such an approach requires extensive preparation and setup. The most probable movements are then rendered on an avatar or communicated to a physical prosthetic limb to influence its movements.

Systems and methods of the present disclosure may be used in conjunction with alternative forms of tracking data to assist a user in controlling a prosthetic limb. In essence, the movement of the user's stump is tracked and the movement data captured there is used to establish an expected motion or limit the possible range of motions to a particular subset. This information is then used to help determine the movements executed by the prosthetic.

Systems and methods of the present disclosure provide the player with a valuable visual stimulus that they once again have the missing limb. The player's tracked movements cause the limb to move as if they are in control of the limb. The limb may be able to interact with objects within a game. The combination of visual stimulations, appearance of control, and interactivity helps create an impression that the player has regained their limb. This is especially helpful for people who experience phantom limb pain. The combinations of these sensations may help the player acknowledge that there missing limb is not in pain, that it is not actively being hurt, that the missing hand or foot is relaxed and not constantly tensed (some hand amputees have the sensation that their missing hand is constantly clenched into a tight fist), and may limit telescoping complications.

In addition to adding amputated limbs, systems and methods of the present disclosure may be used to add other extra limbs. For instance, based on the movement of a single shoulder, a player can control two arms that are animated as attached to a single shoulder of the avatar. Likewise, based on the tracked movement of a single knee, a player can control two appendages that are animated as attached to the avatar's knee. The player's tracked limbs determine the movements of the extra limb(s), and through practice the player is able to take control of the extra limb and learn how to move it in sync with the rest of his or her body.

Animating a Representation of the Player in Real-Time

Systems and methods of the present disclosure may provide improved mapping of a user's movements onto an in-game avatar in real-time, whereby the user controls the avatar by moving his or her own body. In typical games, a controller with various buttons is used to control an in-game avatar. The player's inputs are limited and thus the possible movements are limited so it is practical to animate in advance every possible movement and simply display such pre-recorded animations when the associated button is pressed. An animation controlled by a user's body movements is more complicated.

In the typical VR game, a user's hands are tracked for position, and sometimes orientation. This requires the game to capture tracking data at an imperceptible framerate (i.e. 60+ frames per second), compare the most recent frame to one or more earlier frames to determine whether there is movement across said frames, render a frame for an avatar that represents the user's position less than $\frac{1}{60}$th of a second ago, whereby the rendering of a succession of frames creates the appearance of smooth motion. Typically, the hands are tracked for position and orientation and the tracking data for the hand is used as an end effector to enable inverse kinematics to determine the proper position of attached body parts, such as the forearm, upper arm, etc. Hand position animations are typically the bare minimum required for first-person VR games, however hand position in and of itself is unlikely to provide sufficient immersion for players playing third-person VR games. In general, the more the avatar is mapped to the user, the more immersive the experience becomes.

Immersion requires a faithful mapping of the user's movements to the avatar. The user controls the avatar by moving their own body, and thus the avatar may be able to mimic every possible motion the user performs. Having a pre-recorded motion for every possible position is either impractical or impossible. Instead, the animations may be rendered from a set of tools, whose use allows on demand rendering. In some embodiments, systems and methods of the present disclosure utilize numerous pre-recorded 3D models called key poses. The key poses are typically polygon renders of an avatar defined by a plurality of vertices. A user's position at a given point in time is rendered by blending the nearest key poses in proportion to their proximity to the user's tracked position, e.g. vertex animation. In some embodiments, systems and methods of the present disclosure utilizes a skeleton rig, whereby the bones of the skeleton rig are manipulated in the rendering process to position the avatar in a position similar to the user's own position. In alternate embodiments, a combination of vertex and skeletal animation is applied to render an avatar.

Avatar Structure

Systems and methods of the present disclosure may utilize 3D modeling to generate a virtual entity called an avatar. The avatar may be comprised of virtual bones, a virtual skin or mesh, and virtual clothes.

In one example, the avatar includes virtual bones and comprises an internal anatomical structure that facilitates the formation of limbs and other body parts. Skeletal hierarchies of these virtual bones may form a directed acyclic graph (DAG) structure. Bones may have multiple children, but only a single parent, forming a tree structure. Two bones may move relative to one another by sharing a common parent.

Virtual skin may surround the virtual bones as an exterior surface representation of the avatar. The virtual skin may be modeled as a set of vertices. The vertices may include one or more of point clouds, triangle meshes, polygonal meshes, subdivision surfaces, and low-resolution cages. In some embodiments, the avatar's surface is represented by a polygon mesh defined by sets of vertices, whereby each polygon is constructed by connecting at least three vertices.

Each individual vertex of a polygon mesh may contain position information, orientation information, weight information, and other information. The vertices may be defined as vectors within a Cartesian coordinate system, whereby each vertex has a corresponding (x, y, z) position in cartesian space. In alternative embodiments, the virtual bone transformations may be defined as vectors in quaternion space, whereby each bone has a corresponding (1, i, k, j) position in quaternion space. Quaternion representation of rotation for bone transformations beneficially avoids gimbal locks that temporarily reduces a tracked object's degrees of freedom. Gimbal lock is associated with tracking, and, thus, animation errors.

The movement of the avatar mesh vertices with the skeletal structure may be controlled by a linear blend skinning algorithm. The amount each vertex is associated with a specific bone is controlled by a normalized weight value and can be distributed among multiple bones. This is described more fully in the Skeletal Animation section below.

The surface of the avatar is animated with movement according to either vertex animation, skeletal deformation, or a combination of both. Animation techniques include utilization of blendspaces which can concurrently combine multiple drivers to seamlessly and continuously resolve avatar movement. An example of using a blendspace is a strafing movement model that controls foot animation based on avatar forward/backward and left/right movement. Another example is four hand shapes representing finger positions with different wrist or metacarpus positions (in, out, up, down). In both examples each shape or animation pose is blended together depending on the degree to which its driver is currently active, i.e. how much the avatar has moved in world space or the currently tracked position of the wrist. Morph target shapes are stored offsets of affected vertices that can be blended in and combined with skeletal deformation to create more convincing deformation. An example of morph target animation is the bulging of a bicep muscle in response to forearm movement. Key pose interpolation is the skeletal movement of the avatar blending sequentially from pose to pose where the poses are defined by an animator setting key frame values on the bone transforms.

Special Mesh

Special meshes may be implemented to enable some movement animations. Where movement animations are indirectly related to tracking data (e.g. complementary movements), the associated 3D model may be comprised of a mesh topology separate from the remainder of the 3D model. As an example, the hands of the 3D model may be comprised of a separate topology from the remainder of the 3D model. To achieve movement animations, the hand is modified according to vertex animation, skeletal animation, or a combination of such techniques.

Skeleton Animation

Figure 8:
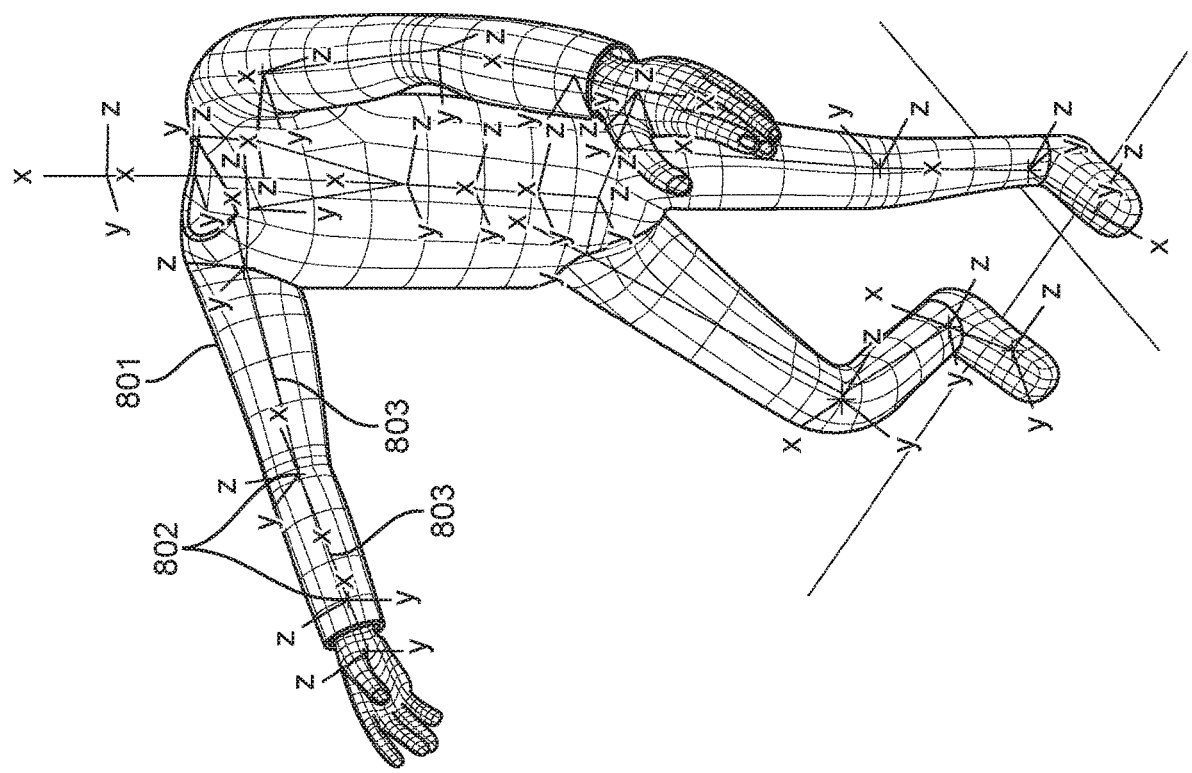
FIG. 8 and FIG. 9 illustrate a 3D model comprised of a mesh fitted with a skeleton, in accordance with some embodiments.
Figure 8:
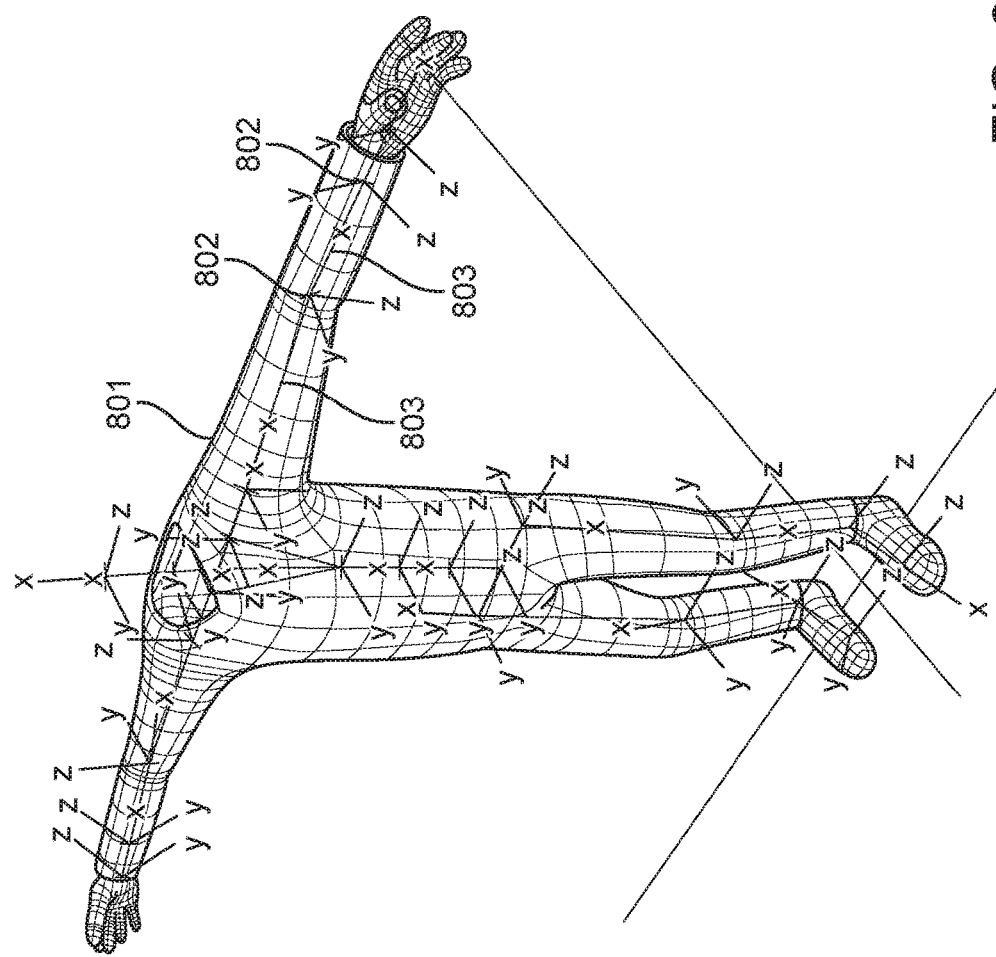
Figure 9:
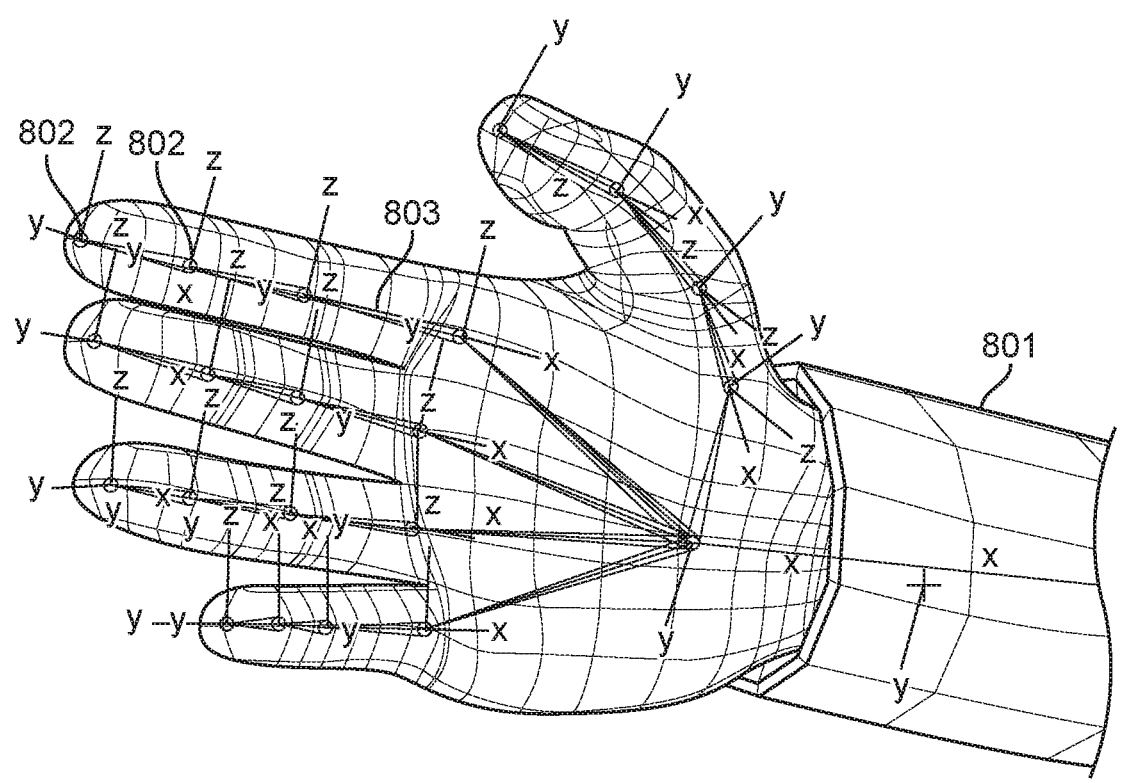

FIG. 8 and FIG. 9 illustrate a 3D model comprised of a mesh fitted with a skeleton. These figures show the mesh 801 as a framework and the skeleton as a hierarchy of pivot points 802 labeled with X, Y, and Z axes where the lines 803 between them indicate the parenting relationship of the bones. Alternatively, these pivot points 802 are labeled with (1, i, k, j) axis labels, which correspond to quaternion coordinates. Each axis may be characterized as a mathematical vector. The parenting relationship allows bones to inherit the motion of their parent bones. The bones of the virtual skeleton may or may not precisely mimic the joints seen in typical human anatomy.

Each bone of the skeleton forms a transformation which influences all vertices associated with the bone. The amount of influence each bone has on each vertex is controlled by a weighting system. In one skeletal animation approach, finger articulation is carefully executed in real-time according to inverse kinematics (with fingertip locations serving as end effectors) to animate intuitive flexions and realistic range of motions for an in-game avatar. For a vertex animation approach, the skeleton of a 3D model is manually manipulated across the joints (or pivot points) to form particular poses of the 3D model. These poses are sometimes called deformations, in that they are deformations of the original 3D model. These deformations are saved as offsets or deltas from the original model in order to be used as key poses for a vertex animation approach.

Vertex Animations

In a vertex animation approach, movement animations may be executed as interpolations between morph targets. A morph target is a new shape created by a copy of the original polygonal mesh with vertex order and topology being maintained and then moving the vertices to create the new desired shape. The morph target is then saved as a set of 3D offsets, one for each vertex, from the original position to the new target position of that vertex. Every deformation made of the model to be animated exists as a key pose or morph target across a variety of triggering mechanisms. For the animation of a hand, movement is animated as an interpolation between the neutral shape and the one or more target shapes. At a basic level applying a morph target is moving each vertex linearly towards its target shape in the direction of the saved offset vector. The amount of activation of the blendshape is controlled by its weight. A weight of 1.0 activates the full target shape. A weight of 0.5 would move each vertex exactly halfway towards the target position. Multiple blendshape targets can be active at once with each controlled by its own weight value. As the weight of blendshapes change over time, smooth interpolation between intermediate shapes is achieved.

To appear realistic, the morph image may be proportionally morphed between its one or more poses. For hand animations, this means that finger movement animations may be animated both in proportion to wrist or metacarpus movement and with the same directionality. This movement is achieved by applying a driver mechanism across each vertex of the polygon mesh. The driver mechanism may execute a mathematical transformation that generates a morph shape that is linearly related to the degree of wrist flexion or has a curved relation to the degree of wrist flexion.

In the case of linear relationship between wrist flexion and finger movement, 25% of wrist flexion from neutral may cause an animation that is 25% deformed towards said key pose and 75% deformed towards the neutral pose. If wrist flexion is angled towards more than one key pose, then hand animations are interpolated proportionate to the proximity of nearby key poses and the neutral pose. For instance, a wrist flexion measurement of 33% "in" and 33% "up" may cause the generation of a hand animation that is interpolated evenly between the hand model's neutral pose, "in" pose, and "up" pose. This middle pose exists within the blend space of these three individual poses.

A curved relationship between wrist flexion and finger movement may generate a different animation for a given wrist flexion when compared to a model utilizing a linear relationship. Assume a hand is moving from the neutral pose to an "in" pose. During the first 25% of wrist flexion, the animation may traverse half the blend space and produce an animation that is 50% "in" and 50% neutral. In this way, the animation driver is accelerated at the front end; showing half the of the hand model's blend space for the first quarter of wrist flexion. The remaining half of the blend space is then slowed down on the back-end and spread out across three quarters of wrist flexion. Of course, this approach may be reversed and hand animations may be slowed on the front-end and accelerated on the back-end.

The vertex animation approach may also utilize easing functions to accommodate rapid movements. Rapid movements may cause an animation technique to temporarily lose accuracy by improperly animating extreme hand poses. Thus, the rate at which a hand may enter or leave a pose is limited by an ease function. The ease functions act to temporarily slow down the display of animated movements. In essence, the ease function generates a lag time in reaching a particular pose when movements are deemed too rapid. In addition, the ease function may avoid animation jerks from gimbaling events that can occur during Cartesian coordinate rotations.

Although animation techniques have been described in reference to wrist, metacarpus, hands, and finger animation, it should be understood that the same animation principles are applicable to other body parts of the avatar. Additionally, the positions determined by such techniques may inform either a specific animation or a specific movement for a prosthetic.

Special Poses and Gestures

In some embodiments, animations may take on more complex movements when the system tracks triggering gestures. For instance, while interacting with a virtual bird within a game, a player's action of reaching out to the bird may trigger the display of a pre-recorded movement animation for the hand of the player's avatar. When tracking data indicates that a player has reached towards a bird with their palms facing upwards, the avatar may be rendered with the palm facing up, and the fingers opening to allow the bird to land. Alternatively, when tracking data indicates that a player has reached towards a bird with their palms facing down, the avatar may be rendered with the palm facing down and the index finger at full extension, while the rest of the fingers are curled in, whereby the bird lands on the avatar's index finger.

Systems and methods of the present disclosure may compare tracking data (across several frames) to a gesture library to identify when a user has performed one or more gestures. The identification of a gesture triggers an animation protocol. Instead of rendering an avatar according to the user's movements, the avatar is rendered according to a combination of the user's movements and one or more pre-recorded animations. The identification of a gesture does not cause the next visualized frame to show the gesture animation. Instead, the gesture animation is introduced gradually. For instance, the last tracked position may be blended with the final gesture position. In some embodiments, the transition between last tracked position and final gesture position takes around one second, whereby the transition is spread across around 60 frames, with each successive frame being rendered with an animation interpolated progressively closer to the final gesture position.

One example of a gesture within the gesture library is a waving gesture. In some embodiments, when tracking data indicates that a user has moved their wrist back and forth while pivoting an otherwise stationary forearm, or as a smooth back and forth arc of the wrist and forearm, the avatar may render a pre-recorded waving animation. In other embodiments, the waving animation is modified to reflect the speed at which the player is moving, modified to reflect the angle of the hand relative to the forearm, and/or modified to match the length of time the gesture is conducted. In essence, the gestures do not wholly take over rendering, instead they are blended with the tracking data, whereby gestures are executed partially according to tracking data and partially according to pre-recorded animations. Optionally, the waving gesture is accompanied with a "hello" audio line.

Figure 10:
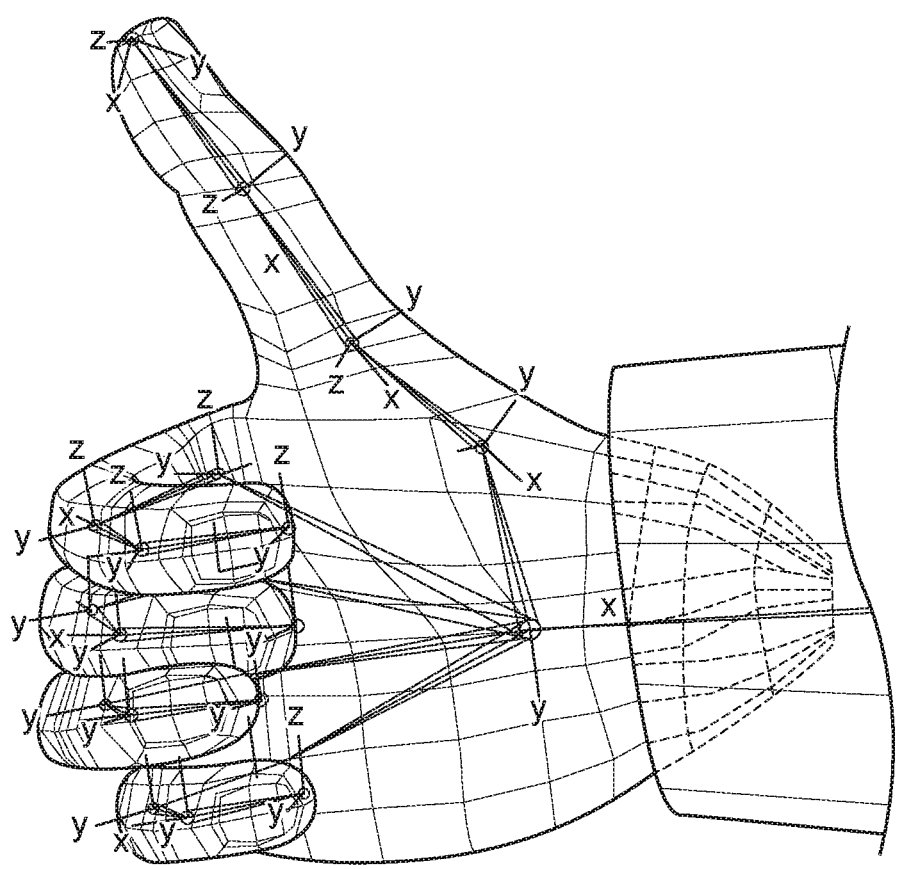
FIG. 10 illustrates a 3D model of a hand taking on the thumbs-up key pose gesture, in accordance with some embodiments.

FIG. 10 illustrates example of a thumbs-up gesture. Here, a 3D model of a hand takes on the thumbs-up key pose gesture via skeletal deformation. In some embodiments, when tracking data indicates that a user has extended their arm and then snapped their wrist down while their thumb is orientated up, then the system renders a pre-recorded thumbs-up motion for however long the pose is held. Similar triggers may be developed for the knees, feet, and toes that may animate things such as kicking a ball or dancing.

The avatar's hands may exhibit motions not directly linked to the player's own motions. For instance, to breathe life into the hands of the avatar, the fingers may splay and stretch at given intervals of non-movement. Such animations may also be displayed for the toes.

The hands may be customized to further improve immersion. The player may choose their gender and gender specific hands may be animated on the avatar. The player may choose a skin tone, finger nail color, and may equip one or more rings. These customizations serve to further increase the player's sense of immersion and take the game one step closer to enabling suspension of disbelief in a virtual world.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for generating complementary tracking data, the system comprising:
   one or a plurality of wearable sensors configured to be disposed on a subject, wherein the wearable sensors are configured to collect and transmit tracking data;
   a processor in communication with a memory that includes processor executable instructions, wherein the execution of the instructions cause the system to:
   (a) receive tracking data from the one or the plurality of wearable sensors;
   (b) map the tracking data onto a 3D model, wherein the 3D model is a virtual representation of an extent and a motion of the subject;
   (c) identify an incomplete portion of the 3D model, the incomplete portion comprising a portion of the model not mapped to the tracking data;
   (d) generate complementary tracking data to substitute for at least a portion of the incomplete portion; and (e) include the complementary tracking data in the 3D model, and
   wherein the memory includes processor executable instructions that cause the system to access one or a series of prior 3D models, wherein the prior 3D models were previously communicated for display.

2. The system of claim 1, wherein the complementary data is generated by comparing available tracking data to a key pose library.

3. The system of claim 1, wherein tracking data is compared to blend spaces between two or more key poses in the key pose library.

4. The system of claim 3, wherein tracking data is compared to key poses of the library of key poses to determine a strongest match.

5. The system of claim 4, wherein the determination of a match weights similarities of joints and body parts closest to the incomplete portion more heavily than joints and body parts distant from the incomplete portion.

6. The system of claim 1, wherein the complementary tracking data is generated by identifying a cluster of repetitive tracking data among a series of prior 3D models, matching tracking data to the cluster, and generating complementary data similar to the matched portion of the cluster.

7. The system of claim 1, wherein the complementary tracking data is generated by identifying a cluster of repetitive tracking data among a series of prior 3D models, determining where available tracking data best fits in the cluster of repetitive tracking data, and generating complementary tracking data that mimics the cluster of repetitive tracking data.

8. The system of claim 1, wherein the processor is configured to analyze the one or a series of prior 3D models for gesture triggers, wherein the identification of a gesture trigger causes the system to communicate a series of updated 3D models that are at least partially blended with a pre-recorded gesture animation.

9. The system of claim 1, wherein complementary tracking data is generated with a FABRIK solver when tracking data for an end effector is available and with a cluster function or key pose match when tracking data for an end effector is unavailable.

10. A system for generating complementary tracking data, the system comprising a processor in communication with a memory that includes processor executable instructions, the instructions comprising:
    a set of tracking data, wherein the tracking data relates to the position or motion of one or more parts of the user;
    a 3D model, wherein the 3D model is a virtual representation of an extent and a motion of a user;
    a library, wherein the library comprises a set of poses, gestures, or both;
    a set of complementary tracking data, wherein the set of complementary tracking data comprises a least a portion of at least one selected pose or gesture from the library;
    a combined model, the combined model comprising the set of tracking data and the set of complementary data, and
    wherein the memory includes processor executable instructions that cause the system to access one or a series of prior 3D models, wherein the prior 3D models were previously communicated for display.

11. The system of claim 10, wherein the complementary data is generated by a comparison of the set of tracking data to a key pose library.

12. The system of claim 11, wherein the comparison comprises spaces between two or more key poses in the key pose library and the complementary data is generated to blend between those spaces.

13. The system of claim 10, wherein complementary tracking data is generated with a FABRIK solver when tracking data for an end effector is available and with a cluster function or key pose match when tracking data for an end effector is unavailable.

14. A system for generating complementary data for a visual display, the system comprising:
    (a) one or more electromagnetic emitters and one or more electromagnetic sensors configured to be selectively placed on one or more tracked body parts; and
    (b) at least one processor in communication with a memory and with the visual display, the one or more electromagnetic emitters, and the one or more electromagnetic sensors and configured to receive tracking data from the one or more electromagnetic emitters and the one or more electromagnetic sensors, and to generate complementary display data comprising projected motion not within the tracking data and based upon a library of potential motions, and
    wherein the memory includes processor executable instructions that cause the system to access one or a series of prior 3D models, wherein the prior 3D models were previously communicated for display.

* * * * *